US011300571B2

(12) United States Patent
Clinton et al.

(10) Patent No.: US 11,300,571 B2
(45) Date of Patent: Apr. 12, 2022

(54) ASSAY APPARATUSES, METHODS AND REAGENTS

(71) Applicant: Meso Scale Technologies, LLC, Gaithersburg, MD (US)

(72) Inventors: Charles M. Clinton, Clarksburg, MD (US); Eli N. Glezer, Chevy Chase, MD (US); Bandele Jeffrey-Coker, Darnestown, MD (US); Sandor L. Kovacs, Middletown, MD (US); Sudeep M. Kumar, Gaithersburg, MD (US); George Sigal, Rockville, MD (US); Carl Stevens, Silver Spring, MD (US); Michael Vock, Loveland, OH (US)

(73) Assignee: Meso Scale Technologies, LLC., Rockville, MD (US)

( * ) Notice: Subject to any disclaimer, the term of this patent is extended or adjusted under 35 U.S.C. 154(b) by 104 days.

(21) Appl. No.: 16/420,724

(22) Filed: May 23, 2019

(65) Prior Publication Data

US 2019/0277855 A1 Sep. 12, 2019

Related U.S. Application Data

(63) Continuation of application No. 11/642,968, filed on Dec. 21, 2006, now Pat. No. 10,302,649.
(Continued)

(51) Int. Cl.
*B01L 3/00* (2006.01)
*G01N 35/02* (2006.01)
(Continued)

(52) U.S. Cl.
CPC .......... *G01N 33/582* (2013.01); *B01L 3/5085* (2013.01); *B01L 3/50255* (2013.01);
(Continued)

(58) Field of Classification Search
None
See application file for complete search history.

(56) References Cited

U.S. PATENT DOCUMENTS 1,689,047 A 10/1928 Packer
4,168,146 A 9/1979 Grubb et al.
(Continued)

FOREIGN PATENT DOCUMENTS

CN 1081512 A 2/1994
CN 1178907 A 4/1998
(Continued)

OTHER PUBLICATIONS

Intl Search Report for PCT/US2006/049049, two pages, dated May 7, 2008.
(Continued)

*Primary Examiner* — Neil N Turk
(74) *Attorney, Agent, or Firm* — Conley Rose, P.C.

(57) ABSTRACT

We describe apparatuses, systems, method, reagents, and kits for conducting assays as well as process for their preparation. They are particularly well suited for conducting automated sampling, sample preparation, and analysis in a multi-well plate assay format. For example, they may be used for automated analysis of particulates in air and/or liquid samples derived therefrom in environmental monitoring.

20 Claims, 10 Drawing Sheets

Related U.S. Application Data

(60) Provisional application No. 60/752,745, filed on Dec. 21, 2005, provisional application No. 60/752,513, filed on Dec. 21, 2005.

(51) Int. Cl.
  *G01N 33/58* (2006.01)
  *B67B 7/00* (2006.01)
  *G01N 35/10* (2006.01)
  *G01N 21/64* (2006.01)
  *G01N 21/66* (2006.01)
  *G01N 33/53* (2006.01)
  *G01N 35/04* (2006.01)

(52) U.S. Cl.
  CPC ........... *B67B 7/24* (2013.01); *G01N 21/6452* (2013.01); *G01N 21/66* (2013.01); *G01N 33/5302* (2013.01); *G01N 35/028* (2013.01); *G01N 35/1011* (2013.01); *G01N 35/1079* (2013.01); *G01N 35/1081* (2013.01); *G01N 35/1002* (2013.01); *G01N 35/109* (2013.01); *G01N 2035/0405* (2013.01); *G01N 2035/0425* (2013.01); *G01N 2035/1025* (2013.01); *Y10T 83/9314* (2015.04)

(56) References Cited

U.S. PATENT DOCUMENTS

| | | |
|---|---|---|
| 4,235,601 A | 11/1980 | Deutsch et al. |
| 4,366,241 A | 12/1982 | Tom et al. |
| 4,442,204 A | 4/1984 | Greenquist et al. |
| 4,450,231 A | 5/1984 | Ozkan |
| 4,704,255 A | 11/1987 | Jolley |
| 4,735,778 A | 4/1988 | Maruyama et al. |
| 4,763,460 A | 8/1988 | Higo et al. |
| 4,770,856 A | 9/1988 | Uthemann et al. |
| 4,803,050 A | 2/1989 | Mack |
| 4,806,313 A | 2/1989 | Ebersole et al. |
| 4,828,386 A | 5/1989 | Matkovich et al. |
| 4,847,050 A | 7/1989 | Jenkins et al. |
| 4,895,706 A | 1/1990 | Root et al. |
| 4,967,604 A | 11/1990 | Arpagaus et al. |
| 4,988,618 A | 1/1991 | Li et al. |
| 4,988,627 A | 1/1991 | Smith-Lewis |
| 5,084,246 A | 1/1992 | Lyman et al. |
| 5,110,556 A | 5/1992 | Lyman et al. |
| 5,208,535 A | 5/1993 | Nakayama et al. |
| 5,279,797 A | 1/1994 | Burns et al. |
| 5,312,744 A | 5/1994 | Shibata |
| 5,378,638 A | 1/1995 | Deeg et al. |
| 5,665,315 A | 9/1997 | Robert et al. |
| 5,766,554 A | 6/1998 | Liu |
| 5,882,602 A | 3/1999 | Savage et al. |
| 5,989,835 A | 11/1999 | Taylor |
| 6,025,985 A | 2/2000 | Leytes et al. |
| 6,033,100 A | 3/2000 | Marquiss et al. |
| 6,071,748 A | 6/2000 | Modlin et al. |
| 6,096,562 A | 8/2000 | Bunn et al. |
| 6,097,025 A | 8/2000 | Modlin et al. |
| 6,103,479 A | 8/2000 | Taylor |
| 6,159,425 A | 12/2000 | Edwards et al. |
| 6,187,267 B1 | 2/2001 | Taylor et al. |
| 6,241,664 B1 | 6/2001 | Carr et al. |
| 6,258,326 B1 | 7/2001 | Modlin |
| 6,270,726 B1 | 8/2001 | Tyberg et al. |
| 6,296,020 B1 | 10/2001 | McNeely et al. |
| 6,297,018 B1 | 10/2001 | French et al. |
| 6,310,687 B1 | 10/2001 | Stumbo et al. |
| 6,313,960 B2 | 11/2001 | Marquiss et al. |
| 6,317,207 B2 | 11/2001 | French et al. |
| 6,326,605 B1 | 12/2001 | Modlin et al. |
| 6,365,110 B1 | 4/2002 | Rainin et al. |
| 6,394,952 B1 | 5/2002 | Anderson et al. |
| 6,413,873 B1 | 7/2002 | Li et al. |
| 6,416,959 B1 | 7/2002 | Giuliano et al. |
| 6,429,026 B1 | 8/2002 | Pettersson et al. |
| 6,466,316 B2 | 10/2002 | Modlin et al. |
| 6,483,582 B2 | 11/2002 | Modlin et al. |
| 6,483,585 B1 | 11/2002 | Yang |
| 6,486,947 B2 | 11/2002 | Modlin et al. |
| 6,495,369 B1 | 12/2002 | Kercso et al. |
| 6,503,719 B2 | 1/2003 | Modlin et al. |
| 6,548,263 B1 | 4/2003 | Kapur et al. |
| 6,567,008 B1 | 5/2003 | Sansone |
| 6,591,852 B1 | 7/2003 | McNeely et al. |
| 6,601,613 B2 | 8/2003 | McNeely et al. |
| 6,630,359 B1 * | 10/2003 | Caillat ............... C12Q 1/001 422/50 |
| 6,635,430 B1 | 10/2003 | Tortorella |
| 6,671,624 B1 | 12/2003 | Dunlay et al. |
| 6,727,071 B1 | 4/2004 | Dunlay et al. |
| 6,756,207 B1 | 6/2004 | Giuliano et al. |
| 6,759,206 B1 | 7/2004 | Rubin et al. |
| 6,783,649 B2 | 8/2004 | Hedberg et al. |
| 6,806,053 B1 | 10/2004 | Sportsman et al. |
| 6,825,921 B1 | 11/2004 | Modlin et al. |
| 6,867,044 B2 | 3/2005 | Cordery et al. |
| 6,887,710 B2 | 5/2005 | Call et al. |
| 6,888,085 B2 | 5/2005 | Spencer et al. |
| 6,902,703 B2 | 6/2005 | Marquiss et al. |
| 6,977,722 B2 | 12/2005 | Wohlstadter et al. |
| 6,982,431 B2 | 1/2006 | Modlin et al. |
| 6,992,761 B2 | 1/2006 | Modlin et al. |
| 7,063,946 B2 | 6/2006 | Kenten et al. |
| 7,117,098 B1 | 10/2006 | Dunlay et al. |
| 7,160,687 B1 | 1/2007 | Kapur et al. |
| 7,198,759 B2 | 4/2007 | Bryning et al. |
| 7,262,858 B2 | 8/2007 | Lin et al. |
| 7,384,779 B2 | 6/2008 | Fang et al. |
| 7,497,997 B2 | 3/2009 | Glezer et al. |
| 7,618,829 B2 | 11/2009 | Keizer et al. |
| 7,807,448 B2 | 10/2010 | Glezer et al. |
| 7,842,246 B2 | 11/2010 | Wohlstadter et al. |
| 7,858,321 B2 | 12/2010 | Glezer et al. |
| 7,981,362 B2 | 7/2011 | Glezer et al. |
| 8,012,745 B2 | 9/2011 | Glezer et al. |
| 8,053,211 B2 | 11/2011 | Dassler et al. |
| 8,298,834 B2 | 10/2012 | Glezer et al. |
| 9,878,323 B2 | 1/2018 | Glezer et al. |
| 2002/0001545 A1 | 1/2002 | Cronenberg et al. |
| 2002/0009391 A1 | 1/2002 | Marquiss et al. |
| 2002/0036018 A1 | 3/2002 | McNeely et al. |
| 2003/0049862 A1 | 3/2003 | He et al. |
| 2003/0059766 A1 | 3/2003 | Goertz et al. |
| 2003/0113713 A1 | 6/2003 | Glezer et al. |
| 2003/0204316 A1 | 10/2003 | Dunlay et al. |
| 2003/0207290 A1 | 11/2003 | Kenten et al. |
| 2004/0022677 A1 | 2/2004 | Wohlstadter et al. |
| 2004/0075566 A1 | 4/2004 | Stepanik et al. |
| 2004/0109793 A1 | 6/2004 | McNeely et al. |
| 2004/0121402 A1 | 6/2004 | Harper et al. |
| 2004/0161368 A1 | 8/2004 | Hotlund et al. |
| 2004/0171087 A1 | 9/2004 | Rech-Weichselbraun et al. |
| 2004/0189311 A1 | 9/2004 | Glezer et al. |
| 2005/0052646 A1 | 3/2005 | Wohlstadter et al. |
| 2005/0142033 A1 | 6/2005 | Glezer et al. |
| 2005/0221281 A1 | 10/2005 | Ho |
| 2005/0223822 A1 | 10/2005 | Ozbal |
| 2005/0266582 A1 | 12/2005 | Modlin et al. |
| 2006/0187017 A1 | 8/2006 | Kulesz et al. |
| 2006/0210435 A1 | 9/2006 | Alavie et al. |
| 2007/0041878 A1 | 2/2007 | Bryning et al. |
| 2007/0105213 A1 | 5/2007 | Bryning et al. |
| 2007/0202538 A1 | 8/2007 | Glezer et al. |
| 2007/0231217 A1 | 10/2007 | Clinton et al. |
| 2007/0269839 A1 | 11/2007 | Goertz et al. |
| 2008/0044928 A1 | 2/2008 | Char et al. |
| 2009/0258415 A1 | 10/2009 | Bryning et al. |
| 2009/0263904 A1 | 10/2009 | Clinton et al. |
| 2011/0015091 A1 | 1/2011 | Glezer et al. |
| 2011/0020178 A1 | 1/2011 | Clinton et al. |
| 2011/0059870 A1 | 3/2011 | Wohlstadter et al. |

(56) References Cited

U.S. PATENT DOCUMENTS

| | | |
|---|---|---|
| 2011/0203924 A1 | 8/2011 | Wohlstadter et al. |
| 2011/0256630 A1 | 10/2011 | Clinton |
| 2011/0269642 A1 | 11/2011 | Glezer et al. |
| 2012/0190590 A1 | 7/2012 | Wohlstadter et al. |
| 2012/0190591 A1 | 7/2012 | Wohlstadter et al. |

FOREIGN PATENT DOCUMENTS

| | | |
|---|---|---|
| CN | 2296009 Y | 10/1998 |
| CN | 1224500 A | 7/1999 |
| CN | 1248495 A | 3/2000 |
| CN | 2441811 Y | 8/2001 |
| CN | 1354673 A | 6/2002 |
| CN | 1526074 A | 9/2004 |
| CN | 1549921 A | 11/2004 |
| CN | 1629639 A | 6/2005 |
| CN | 2720448 Y | 8/2005 |
| DE | 3411656 A1 | 10/1985 |
| EP | 0198413 A2 | 10/1986 |
| EP | 0245920 A2 | 11/1987 |
| EP | 0321260 A1 | 6/1989 |
| EP | 0500506 A1 | 8/1992 |
| EP | 0947831 | 10/1999 |
| EP | 1384987 A2 | 1/2004 |
| EP | 1447454 | 8/2004 |
| EP | 1568986 A1 | 8/2005 |
| JP | 62-79164 U | 5/1987 |
| JP | 62-273456 A | 11/1987 |
| JP | 63-205566 A | 8/1988 |
| JP | 01259257 A | 10/1989 |
| JP | 02269599 A | 11/1990 |
| JP | 05329384 A | 12/1993 |
| JP | 0749349 A | 2/1995 |
| JP | 07209693 A | 8/1995 |
| JP | 07218513 A | 8/1995 |
| JP | H08-105900 | 4/1996 |
| JP | 08266639 A | 10/1996 |
| JP | 08301322 A | 11/1996 |
| JP | 0912064 A | 1/1997 |
| JP | 10142227 A | 5/1998 |
| JP | 11326340 A | 11/1999 |
| JP | 11337557 A | 12/1999 |
| JP | 2000505892 A | 5/2000 |
| JP | 2000509486 A | 7/2000 |
| JP | 2001188044 A | 7/2001 |
| JP | 2001255327 A | 9/2001 |
| JP | 2002-181837 | 6/2002 |
| JP | 2002525574 A | 8/2002 |
| JP | 2002535620 A | 10/2002 |
| JP | 2003506697 A | 2/2003 |
| JP | 2003522318 A | 7/2003 |
| JP | 2004003916 A | 1/2004 |
| JP | 2004527758 A | 9/2004 |
| JP | 2004-534226 | 11/2004 |
| JP | 2004325398 A | 11/2004 |
| JP | 2005-37179 | 2/2005 |
| JP | 2005134372 A | 5/2005 |
| JP | 2005513441 A | 5/2005 |
| JP | 2005521032 A | 7/2005 |
| JP | 2005534044 A | 11/2005 |
| JP | 5885788 B2 | 3/2016 |
| WO | 1986002168 | 4/1986 |
| WO | 1989005978 | 6/1989 |
| WO | 1997027483 | 7/1997 |
| WO | 1997038311 | 10/1997 |
| WO | 1998022823 | 5/1998 |
| WO | 1999045360 | 9/1999 |
| WO | 2000016085 A1 | 3/2000 |
| WO | 2000042432 A1 | 7/2000 |
| WO | 2001011310 A1 | 2/2001 |
| WO | 2001028683 | 4/2001 |
| WO | WO 03/001889 | 1/2003 |
| WO | 2003023360 | 3/2003 |
| WO | 2003052428 | 6/2003 |
| WO | 2003061832 | 7/2003 |
| WO | 2004011147 A1 | 2/2004 |
| WO | 2004061418 A2 | 7/2004 |
| WO | 2005024436 A1 | 3/2005 |
| WO | 2005062050 A1 | 7/2005 |
| WO | WO 2005/100945 | 10/2005 |
| WO | 2006094388 A1 | 9/2006 |

OTHER PUBLICATIONS

Int'l Preliminary Report on Patentability for PCT/US2006/049049, eight pages, completed Mar. 19, 2009.
International Search Report for PCT/US2009/002244, six pages (dated Nov. 2009).
Notification of Reason for Rejection for related Japanese Application, Serial No. 2008-547613, three pages (dated Jan. 2012).
Takami, Notification of Reasons for Rejection in JP 2012-158378, three pages (dated Jan. 2014) along with English translations of the examination report and the pending JP claims (in lieu of an English translation of the Japanese patent application cited by the JPO, its concise explanation of the relevance and what is believed to be a US counterpart are provided).
Int'l Search Report for PCT/US2006/049048 dated Dec. 11, 2007 (3 pages).
Written Opinion for PCT/US2006/049048 dated Dec. 11, 2007 (7 pages).
Int'l Preliminary Report on Patentability for PCT/US2006/049048 dated Jun. 24, 2008 (7 pages).
Int'l Preliminary Report on Patentability for PCT/US2009/002244 dated Oct. 12, 2010 (5 pages).
Notification of Reason for Rejection in JP 2008-547612 dated Feb. 2012 (4 pages).
Notification of Reasons for Rejection in JP 2012-179913 dated Jan. 14, 2014 (7 pages).
Japanese Patent Application No. 2017-85775 Notification of Reason for Rejection dated Feb. 27, 2018 (7 pages).
Examination Report in Canadian Application No. 3,006,231 dated Mar. 22, 2019 (3 pages).
Chinese Patent Application No. 201510416789.3 Office Action dated Jun. 2, 2017 (10 pages).
First Office Action and Search Report in CN 201210109497.1 dated Mar. 25, 2014 (10 pages).
Supplementary European Search Report and European Search Opinion for EP 06846006.2 dated Apr. 10, 2014 (11 pages).
Supplementary European Search Report and Search Opinion for EP 15193494.0 dated May 12, 2016 (6 pages).
Extended European Search Report in European Application No. 18191510.9 dated Oct. 8, 2018 (9 pages).
Qin et al. "Time-resolved fluorescence resonance energy transfer assay for point-of-care testing of urinary albumin" Clinical Chemistry, vol. 49, No. 7, pp. 1105-1113 (Jul. 2003).
Thorpe et al. "A stable lyophilized reagent for use in a potential reference assay for quantitation of anti-D in immunoglobulin products" Biologicals, vol. 30, No. 4, pp. 315-321 (Dec. 2002).
Verkman "Drug Discovery in Academia" Am. J. Physiol. Cell Physiol. 286:465-474 (2004) (11 pages).
Chinese Patent Application No. 201810521786.X Decision of Rejection dated Aug. 12, 2021 (7 pages).

* cited by examiner

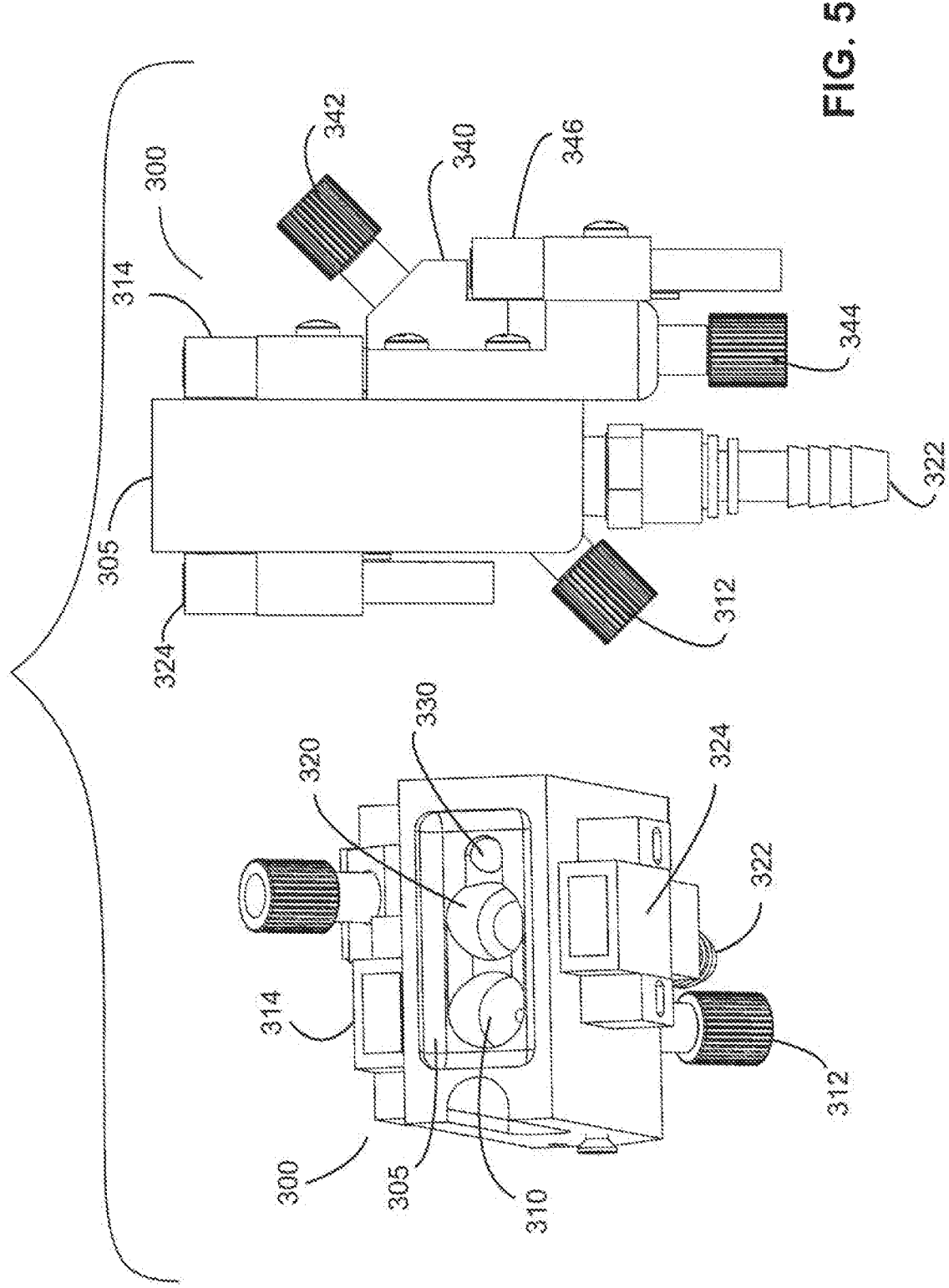

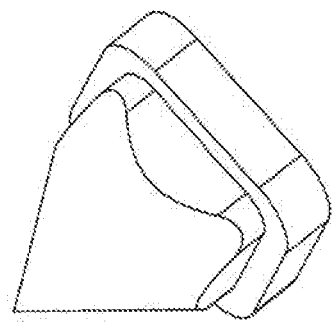
FIG. 7c
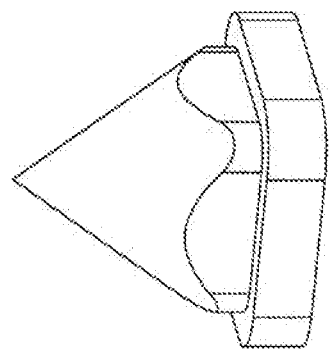
FIG. 7d
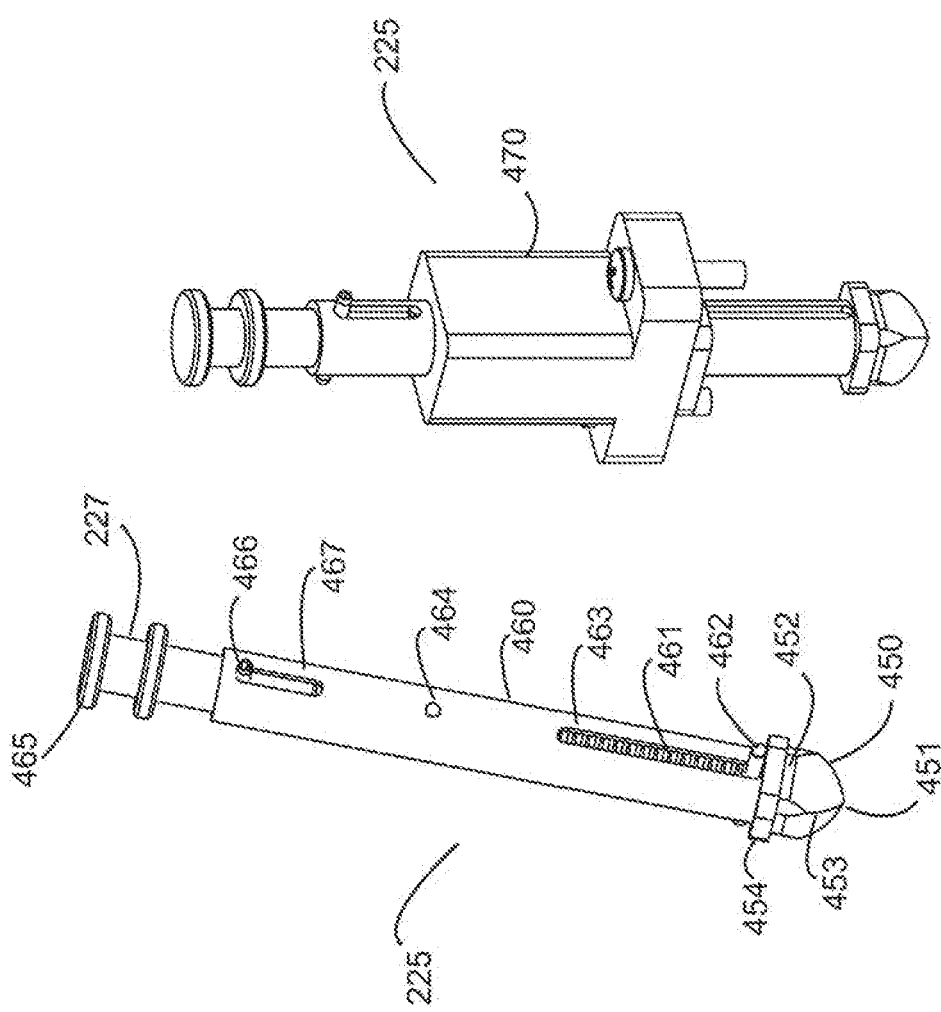
FIG. 7b
FIG. 7a

ASSAY APPARATUSES, METHODS AND REAGENTS

CROSS REFERENCE TO RELATED APPLICATIONS

This application is a continuation of U.S. patent application Ser. No. 11/642,968 filed Dec. 21, 2006, now U.S. Pat. No. 10,302,649 issued May 28, 2019, which claims priority benefit of U.S. Provisional Application No. 60/752,745, filed Dec. 21, 2005 and U.S. Provisional Application No. 60/752,513, filed Dec. 21, 2005; each of which are incorporated by reference.

STATEMENT REGARDING FEDERALLY-SPONSORED RESEARCH

This invention was made with federal support under HDTRA1-05-C-0005 awarded by the Department of Defense. The U.S. government has certain rights in the invention.

FIELD OF THE INVENTION

The invention relates to apparatuses, systems, methods, reagents, and kits for conducting assays. Certain embodiments of the apparatuses, systems, methods, reagents, and kits of the invention may be used for conducting automated sampling, sample preparation, and/or sample analysis in a multi-well plate assay format. For example, they may be used for automated analysis of particulates in air and/or liquid samples derived therefrom.

BACKGROUND OF THE INVENTION

Numerous methods and systems have been developed for conducting chemical, biochemical, and/or biological assays. These methods and systems are essential in a variety of applications including medical diagnostics, food and beverage testing, environmental monitoring, manufacturing quality control, drug discovery, and basic scientific research.

Multi-well assay plates (also known as microtiter plates or microplates) have become a standard format for processing and analysis of multiple samples. Multi-well assay plates can take a variety of forms, sizes, and shapes. For convenience, some standards have appeared for instrumentation used to process samples for high-throughput assays. Multi-well assay plates typically are made in standard sizes and shapes, and have standard arrangements of wells. Arrangements of wells include those found in 96-well plates (12×8 array of wells), 384-well plates (24×16 array of wells), and 1536-well plates (48×32 array of wells). The Society for Biomolecular Screening has published recommended microplate specifications for a variety of plate formats (see http://www.sbsonline.org).

A variety of plate readers are available for conducting assay measurements in multi-well plates including readers that measure changes in optical absorbance, emission of luminescence (e.g., fluorescence, phosphorescence, chemiluminescence, and electrochemiluminescence), emission of radiation, changes in light scattering, and changes in a magnetic field. U.S. Patent Application Publications 2004/0022677 and 2005/0052646 of U.S. patent application Ser. Nos. 10/185,274 and 10/185,363, respectively, of Wohlstadter et al. describe solutions that are useful for carrying out singleplex and multiplex ECL assays in a multi-well plate format. They include plates that comprise a plate top with through-holes that form the walls of the wells and a plate bottom that is sealed against the plate top to form the bottom of the wells. The plate bottom has patterned conductive layers that provide the wells with electrode surfaces that act as both solid phase supports for binding reactions as well as electrodes for inducing electrochemiluminescence (ECL). The conductive layers may also include electrical contacts for applying electrical energy to the electrode surfaces.

Despite such known methods and systems for conducting assays, improved apparatuses, systems, methods, reagents, and kits for conducting automated sampling, sample preparation, and/or sample analysis in a multi-well plate assay format are needed.

SUMMARY OF THE INVENTION

We describe apparatuses for conducting assays in a multi-well plate format that have one or more of the following desirable attributes: i) high sensitivity, ii) large dynamic range, iii) small size and weight, iv) array-based multiplexing capability, v) automated operation (including sample and/or reagent delivery); vi) ability to handle multiple plates, and vii) ability to handle sealed plates. We also describe components that are useful in such an apparatus, and methods for using such an apparatus and components. They are particularly well suited for, although not limited to, use for autonomous analysis of environmental, clinical, or food samples. The apparatus and methods may be used with a variety of assay detection techniques including, but not limited to, techniques measuring one or more detectable signals. Some of them are suitable for electrochemiluminescence measurements and, in particular, embodiments that are suitable for use with multi-well plates with integrated electrodes (and assay methods using these plates) such as those described in U.S. Publications 2004/0022677 and 2005/0052646 of U.S. application Ser. Nos. 10/185,274 and 10/185,363, respectively, of Wohlstadter et al., and the concurrently filed U.S. application Ser. No. 11/624,970 of Glezer et al. entitled "Assay Modules Having Assay Reagents and Methods of Making and Using Same."

An apparatus is provided for measuring a signal from wells of sealed multi-well assay plates comprising a) a seal removal tool for removing seals from wells of the multi-well plates, and b) a detection system for measuring the signal from wells of said multi-well plate. The seal removal tool may function by i) piercing sealing films with a probe with a seal piercing tip, ii) grabbing and removing caps on wells, iii) peeling sealing films from the tops of wells, or iv) removing the seal with a coring tool.

In one embodiment, the seal removal tool is a piercing probe that comprises i) a piercing section with external surfaces that taper to a vertex so as to form a piercing tip at one end of a piercing direction (the axis of translation during a piercing operation) and ii) a seal displacement section, arranged adjacent to the piercing section along the piercing direction. In certain specific embodiments, the seal displacement section has a cross-sectional shape, perpendicular to the piercing direction, that is selected to substantially conform to the shape of the openings of the wells on which the probe will operate. The probe may be slightly undersized relative to the well opening so as to allow the probe to slide into the well opening, and press or fold the pierced seal against the well walls. Such an approach may be used to remove the seal as a barrier to detecting assay signals in the well using detectors (for example, light detectors and/or light imaging systems) situated above the well. The appropriate clearance may be selected based on the thickness of a specific film and/or may be selected to be less than about 0.1 inches, less than about 0.2 inches, or less than about 0.3 inches.

In one example of a piercing tool, the cross-sectional shape of the seal displacement section is a circle. In another example, it is a square or a square with rounded corners. The piercing section may be conical in shape. Alternatively, it may include exposed cutting edges that, e.g., extend in a radial direction from the tip and can act to cut the seal during piercing and aid in reproducibly folding the seal against the well walls. In one specific example, the tip is pyramidal in shape, the edges of the pyramid providing exposed cutting edges.

In certain embodiments, the piercing probe is spring loaded such that the maximal downward force, along said piercing direction, of the probe on a plate seal is defined by the spring constant of a spring. The probe may also comprise a plate stop section adjacent to said seal displacement section that defines the maximum distance of travel of said piercing probe into said wells. In one specific example, the stop section is a region of the probe with a width that is too large to enter a well and the maximum distance is defined by the distance at which the stop section hits the top of the well.

The apparatus may further comprise a pipetting probe. In one embodiment, the piercing probe has a through-hole parallel to the piercing direction. The through-hole is, optionally, off-set from the piercing tip, and the pipetting probe is movably located in the through-hole such that it can be withdrawn into the piercing probe when the piercing probe is being used to remove a well seal and it can be extended from the piercing probe during pipetting operations. The piercing probe and pipetting probe may be controlled independently, e.g., by separate motors. Alternatively, one motor may be used to drive both probes. In one example, the piercing probe comprises a plate stop section as described above and the pipetting probe is coupled to the piercing probe by a spring. The spring is selected to have a spring constant such that i) when the probes are not exerting force on an object, the pipetting probe is withdrawn into the through-hole in the piercing probe, ii) translation of the pipetting probe toward a well results in the cotranslation of the piercing probe and allows for the delivery of sufficient force to displace a seal on the well, and iii) continued translation past the maximal distance of travel of the piercing probe results in compression of the spring and extension of the pipetting probe from the piercing probe into said well where it may be used to pipette liquids into and out of the well.

A method is provided of using the apparatuses comprising seal removal tools (described above), the method comprising removing a seal from a well of a multi-well plate and detecting said signal from said well. Removing a seal may include piercing the seal on a well of a multi-well plate and, optionally, cutting the seal into sections (e.g., with using cutting edges on a piercing tip) and folding the sections against the internal walls of the well. The method may further include one or more of: pipetting a sample into the well, pipetting an assay reagent into the well, removing a liquid from the well, washing the well, illuminating the well, or applying an electrical potential to electrodes in the well. Additionally, the method may further comprise repeating some portion or all of the process described above on one or more additional wells of the plate.

A reagent cartridge is provided which may be used to deliver reagent used by and store waste generated by a multi-well plate analysis apparatuses. According to one embodiment, a reagent cartridge comprises a cartridge body that encloses an internal volume. The cartridge body has a reagent port and a waste port for delivering reagent and receiving waste. The reagent cartridge also comprises reagent and waste compartments in the cartridge body that are connected, respectively, to the reagent and waste ports. The volume of the compartments are adjustable such that the relative proportion of the volume of the cartridge body occupied by reagent and waste can be adjusted, e.g., as reagent is consumed in assays and returned to the cartridge as waste. The total internal volume of the cartridge body may be less than about 2, less than about 1.75, less than about 1.5, or less than about 1.25 times the volume of liquid stored in the body, e.g., the volume of reagent originally provided in the cartridge, thus minimizing the space required for waste and reagent storage, and allowing for convenient one-step reagent replenishment and waste removal. In certain embodiments, the apparatus has a reagent cartridge slot configured to receive the cartridge, and provide fluidic connection to the waste and reagent ports, optionally via "push-to-connect" or "quick connect" fittings.

The reagent and waste compartments may be provided by collapsible bags located in the cartridge body. Alternatively, one of the reagent and waste compartments may be provided by a collapsible bag and the other may be provided by the cartridge body itself (i.e., the volume in the cartridge body excluding the volume defined by any collapsible bags in the cartridge body). In addition to the first reagent and waste compartments, the reagent cartridge may further comprise one or more additional collapsible reagent and/or waste compartments connected to one or more additional reagent and/or waste ports.

Methods of using the reagent cartridges are provided. The method comprises removing reagent from the reagent compartment and introducing waste into the waste compartment. In certain embodiments, at least about 70%, at least about 80%, or at least about 90% of the reagent volume is reintroduced into the reagent cartridge as waste.

Liquid dispensers are provided. The dispenser may be used to add or remove liquids from the wells of a multi-well plate. An assay apparatus is provided that includes the dispenser. One embodiment of the liquid dispenser comprises a pipetting probe comprising a vertical tube element. The dispenser also comprises a probe guide that supports the tube element in a vertical orientation, and configured to allow said tube element to move vertically in the guide between a fully extended position and a fully retracted position. The dispenser further comprises a spring element coupled to the vertical tube element and probe guide that biases the tube element to the fully extended position (i.e., extended downward). A vertical translation stage is attached to the probe guide to raise and lower the probe.

The tube element has a lower opening through which fluid is dispensed or aspirated. In one embodiment, the lower opening is a blunt tube end. Optionally, the end may be slotted to allow movement of fluid through the opening when the opening is pressed against a flat surface. In certain embodiments, the dispenser comprises two or more tube elements. In one specific example different reagents are dispensed through different tube elements. In another specific example, one tube element is used to dispense reagent and another tube element is used to aspirate waste. Multiple tube elements may be configured in a variety of arrangements, for example, as parallel tubes or concentric tubes.

A method is provided for using the liquid dispenser for adding or withdrawing fluid from a container, e.g., a well of a multi-well plate. One method comprises a) lowering the pipetting probe into the container by lowering the translation stage until the probe touches a bottom surface of the container, b) continuing to lower the translation stage such that said tube element pushes against the spring and retracts into the probe guide to a position between said fully extended and fully retracted positions, c) adding fluid to and/or withdrawing fluid from the container through the pipetting probe, and d) raising the pipetting probe out of said container by raising said translation stage.

In a specific embodiment employing a container with a piercable seal, the method may further comprise lowering the translation stage until the probe contacts and pierces the seal. In addition, piercing the seal may further comprise e) lowering the translation stage until the pipetting probe contacts the plate seal, f) continuing to lower the translation stage such that the tube element pushes against the spring and retracts in the probe guide to the fully retracted position, and g) continuing to lower the translation stage such that the pipetting probe pierces the plate seal and the tube element returns to the fully extended position.

An apparatus is provided for conducting luminescence assays in multi-well plates. One embodiment comprises a light-tight enclosure that provides a light-free environment in which luminescence measurements may be carried out. The enclosure includes a plate translation stage for translating a plate horizontally in the enclosure to zones where specific assay processing and/or detection steps are carried out. The enclosure also includes an enclosure top having one or more plate introduction apertures through which plates may be lowered onto or removed from the plate translation stage (manually or mechanically). A sliding light-tight door is used to seal to the plate introduction apertures from environmental light prior to carrying out luminescence measurements.

The apparatus may also comprise a light detector which may be mounted within the light-tight enclosure or, alternatively, it may be mounted to a detection aperture on the enclosure top (e.g., via a light-tight connector or baffle). In certain embodiments, the light detector is an imaging light detector such as a CCD camera and may also include a lens. The apparatus may also comprise pipetting systems, seal piercing systems, reagent and waste storage containers, tube holders for sample or reagent tubes, fluidic stations for delivering/removing samples/reagents/waste, etc. These components may be conventional components such as components known in the art. Alternatively, the apparatus may employ specific components as described herein. Furthermore, the apparatus may comprise computers or other electronic systems for controlling operation the apparatus including, e.g., operating motorized mechanical systems, and triggering and/or analyzing luminescence signals.

Another embodiment of an apparatus for conducting luminescence assays in multi-well plates comprises a light-tight enclosure comprising i) one or more plate elevators having plate lifting platforms that can be raised and lowered, ii) a light-tight enclosure top having one or more plate introduction apertures positioned above the plate elevators and a detection aperture, the enclosure top comprising a sliding light-tight door for sealing the plate introduction apertures, and iii) a plate translation stage for translating a plate in one or more horizontal directions. The plate translation stage comprises a plate holder for supporting the plate which has an opening under the plate to allow plate elevators positioned below the plate holder to access and lift the plate. Furthermore, the plate translation stage being configured to position plates below the detection aperture and to position the plates above the plate elevators.

The apparatus further comprises one or more plate stackers and a light detector. The plate stackers are mounted on the enclosure top above the plate introduction apertures and are configured to receive plates from or deliver plates to the plate elevators. The light detector is mounted on the enclosure top and coupled to the imaging aperture with a light-tight seal.

Certain specific embodiments of the apparatus may further comprise a pipetting system for delivering liquids to or removing liquids from the wells of an assay plate in the apparatus. In one specific embodiment, the pipetting system comprises a pipetting probe mounted on a pipette translation stage for translating said pipetting probe in a vertical direction and, optionally, in one or more horizontal directions. Furthermore, the enclosure top has one or more pipetting apertures and the sliding light-tight door has one or more pipetting apertures. The sliding light-tight door has a pipetting position where the pipetting apertures in the enclosure top align with the pipetting apertures in the sliding light-tight door. The pipette translation stage is mounted on the enclosure top and configured such that, when the sliding light-tight door is in the pipetting position, the pipetting probe may be lowered to access wells positioned under the pipetting apertures in the enclosure top.

Another optional component of the apparatus is a seal removal tool such as a plate seal piercing probe. In one example, the enclosure top and sliding light-tight door have piercing probe apertures and the light-tight door has a piercing position where the piercing apertures in the door and top align. The piercing probe is mounted on the enclosure top and configured such that, when the sliding light-tight door is in the piercing position, the piercing probe may be lowered so as to pierce seals on wells positioned under the piercing apertures in the enclosure top. Advantageously, when both the piercing probe and the pipette probe are present, both may be driven with a single translation stage, e.g., as described above for the integrated pipetting/piercing tool. In an alternate embodiment, a pipette translation stage supporting the pipette probe comprises a probe translation element and the pipette translation stage is configured to travel horizontally and grab the piercing probe with the probe translation element, and to travel vertically to lower and raise said piercing probe.

Additional optional components of the apparatus are plate contacts for making electrical contact to the plates and providing electrical energy to electrodes in wells positioned under said light detector (e.g., for inducing ECL).

A method is also provided for using the apparatus for conducting luminescence assays in multi-well plates. The plates may be conventional multi-well plates. In certain embodiments, plates adapted for use in electrochemiluminescence assays are employed as described in U.S. application Ser. Nos. 10/185,274; 10/185,363; and 10/238,391. In assay methods that detect ECL from one well at a time, the electrode and electrode contacts in these wells are adapted to allow application of electrical energy to electrodes in only one well at a time. The apparatus my be particularly well-suited for carrying out assays in plates containing dry reagents and/or sealed wells, e.g., as described in concurrently filed U.S. application Ser. No. 11/624,970 of Glezer et al. entitled "Assay Modules Having Assay Reagents and Methods of Making and Using Same."

In one embodiment, the method comprises: a) introducing a plate to a plate stacker, b) opening the light-tight door, c) lower the plate from the plate stacker to the plate holder on the plate translation stage, d) sealing the light-tight door, e) translating the plate to position one or more wells under the light detector, e) detecting luminescence from the one or more wells, f) opening the light-tight door, g) translating the plate to a position under a plate stacker, and h) raising the plate to the plate stacker. The method may further comprising translating said plate carriage to position one or more additional wells under said light detector and detecting luminescence from said one or more additional wells. The method may also, optionally, comprise one or more of: i) pipetting sample/or reagent into or out of one of said wells, ii) removing seals from one or more of said wells, or iii) applying electrical energy to electrodes in one or more of said wells (e.g., to induce electrochemiluminescence).

Where the apparatus comprises a pipetting probe, and the enclosure top and sliding door includes pipetting apertures, the method may further comprise: sliding the sliding light-tight door to the pipetting position and using the pipetting probe to introduce and/or remove reagent and/or sample from one or more wells of the plate. Where the apparatus comprises a seal piercing probe, and the enclosure top and sliding door includes piercing apertures, the method may further comprise: sliding the sliding light-tight door to the piercing position, aligning a well of the plate under the piercing probe, and piercing a seal on the well. They may be repeated to seal additional wells of the plate. In one embodiment, a seal on a well of a plate is pierced with the seal piercing tool prior to being accessed by a pipetting probe. In another embodiment, the well is first accessed by a pipetting probe (which pierces the seal to form one or more small holes or tears in the seal. The well is then subsequently pierced with the piercing probe to fully displace the seal and allow for unencumbered detection of signal from the well.

The light detector may be a conventional light detector such as a photodiode, avalanche photodiode, photomultiplier tube, or the like. Suitable light detectors also include arrays of such light detectors. Light detectors that may be used also include imaging systems such as CCD and CMOS cameras. The light detectors may also include lens, light guides, etc. for directing, focusing and/or imaging light on the detectors. In certain specific embodiments, an imaging system is used to image luminescence from arrays of binding domains in one or more wells of an assay plate and the assay apparatus reports luminescence values for luminescence emitted from individual elements of said arrays.

An environmental monitoring system is also provided that comprise an analyte detection module and an air sampling system. The air sampling system processes air to concentrate particulate matter in the air and suspend the particulates in a liquid suspension. The detection module is an apparatus for conducting luminescence assays in multi-well plates as disclosed herein. In operation, the air sampling system processes air for a certain period of time and delivers sample to the analyte detection module, which then carries out assays for one or more target analytes in one or more wells of an assay plate and, on completion of the assay, reports results. The air sampling system, detection module, and interface between the two components, preferably, is designed to operate in an autonomous fashion. At selected intervals of time, additional samples are delivered from the air sampling system to the detection module and analyzed in unused wells of the assay plate. The assays may be scheduled to be run in a serial fashion. Alternatively, the assays may be scheduled to be run in a staggered fashion in which some steps overlap. Through the use of multi-well plates (and plate stackers that hold multiple multi-well plates) long periods of autonomous operation can be achieved without requiring replenishment of consumables.

BRIEF DESCRIPTION OF DRAWINGS

FIG. 5 shows an embodiment of a sample/waste station 300.

FIGS. 7a-7b show an embodiment of a plate seal piercing probe 225.

FIGS. 7c-7d show an alternative embodiment of the piercing tip that is conical.

DESCRIPTION OF SPECIFIC EMBODIMENTS OF THE INVENTION

Figure 1:
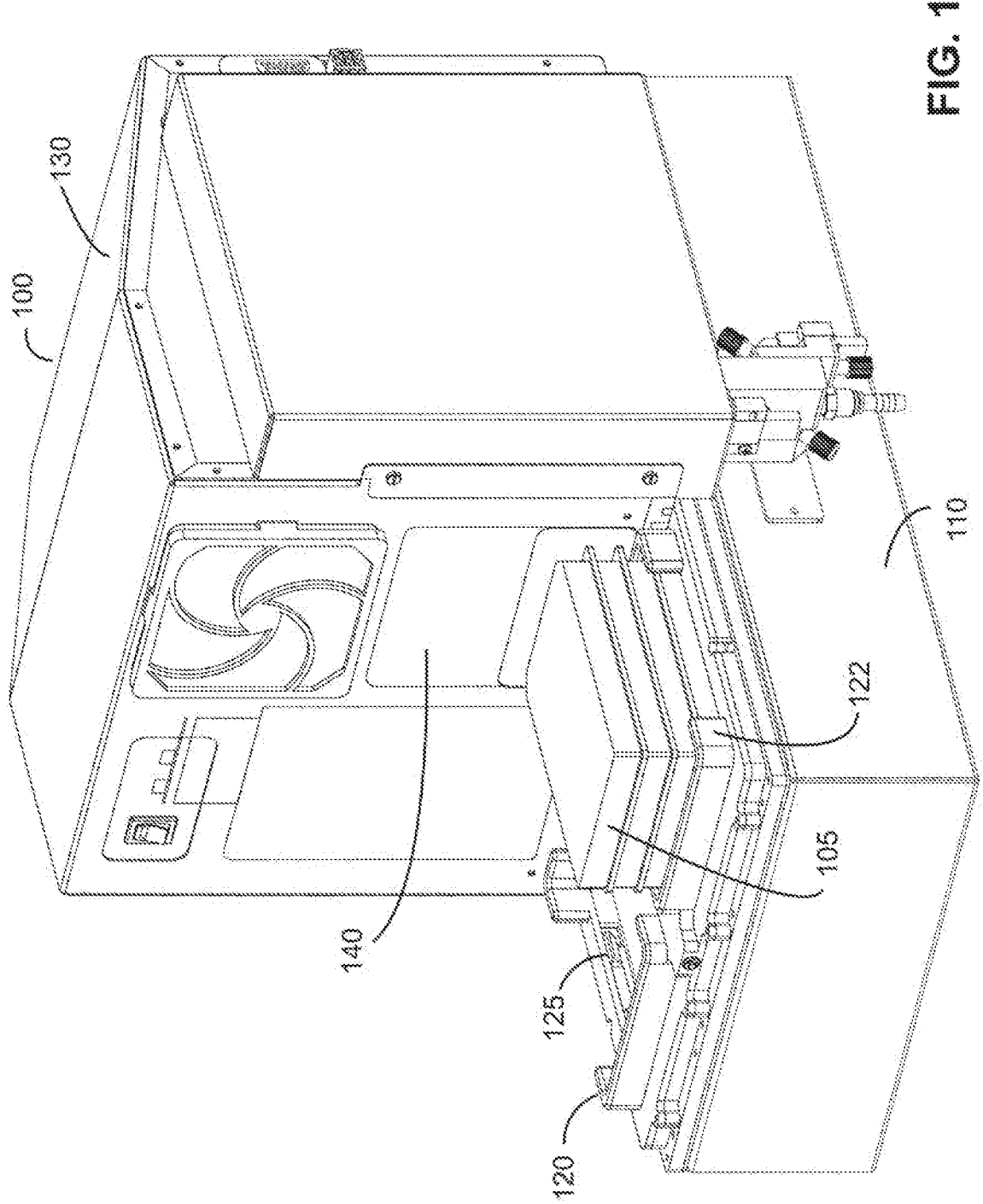
FIG. 1 shows an assembled view of multi-well plate reader 100.

The Detailed Description section provides descriptions of certain embodiments of the invention that should not be considered limiting but are intended to illustrate certain inventive aspects. FIG. 1 shows an isometric view of one embodiment of multi-well plate reader 100. Plate reader 100 has a light-tight enclosure 110 and a fluidic/imaging system enclosure 130. Input and output plate stackers 122 and 120, respectively, hold plates 105 for use in assays (plates are shown as having optional plate seals). Plate stackers 120 and 122 have plate release latches 125 that are spring loaded to allow plates raised from the light-tight enclosure below (using a plate elevator that is not shown in this view) to be captured in the stack. The latches in the input stack 122 can also be directed to be released to allow plates to be released from the stack to a plate elevator below (not shown). Window 140 provides an optical path for a bar code reader in fluidic/imaging system enclosure 130 to read bar codes on plates in input stacker 122. Optionally, a plate stack cover (not shown) may be mounted over the plate stack to protect plates in the stacks from the environment. The plate stack cover may include heaters and/or coolers (e.g., a thermoelectric heater/cooler) and/or a desiccant chamber to maintain the plate stack under controlled temperature and/or humidity.

Figure 2:
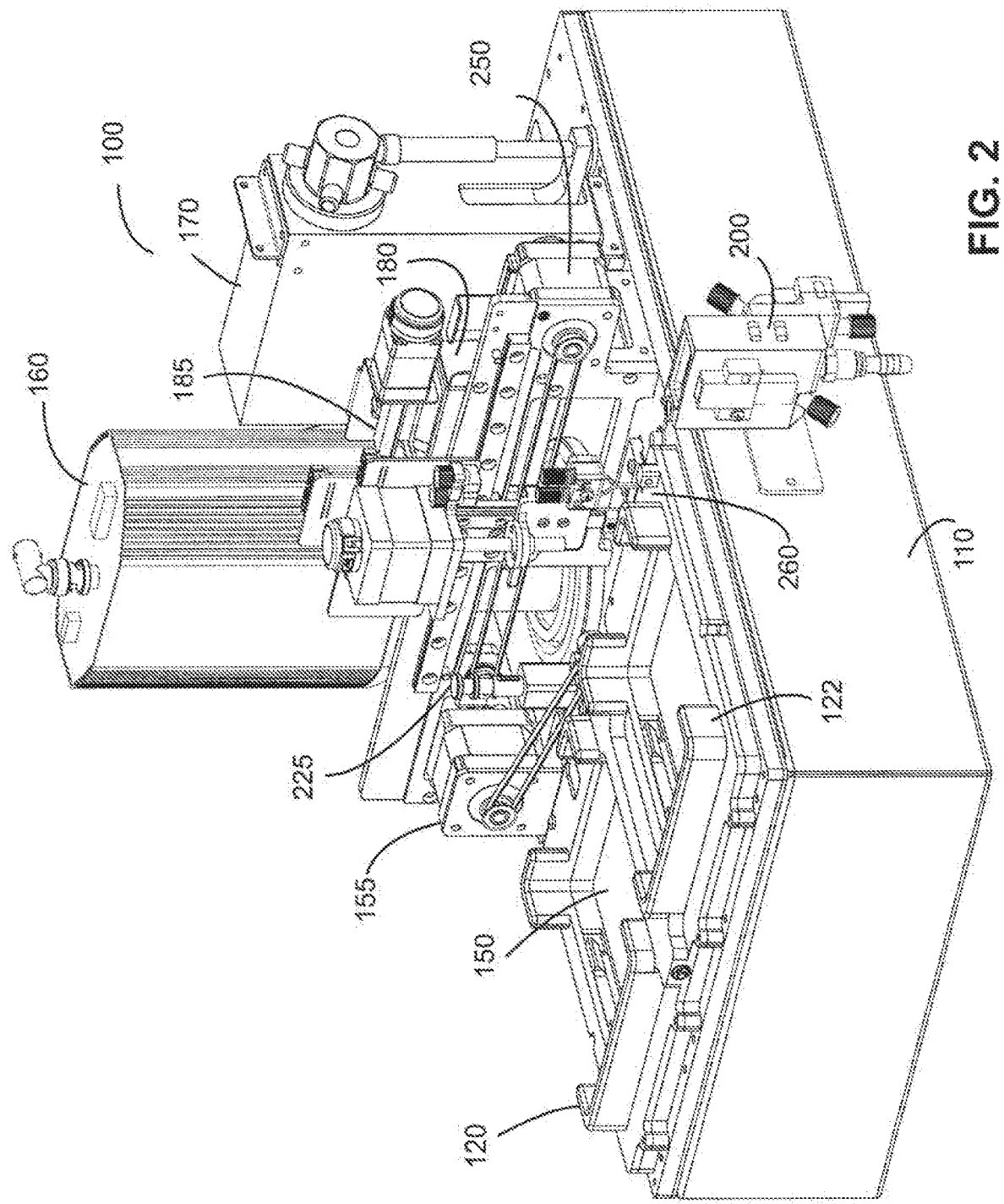
FIG. 2 shows a view of plate reader 100 that exposes embodiments of the light detection and fluidic components.

FIG. 2 is a view of plate reader 100 without the cover of fluidic/imaging system enclosure 130 and plates 105. The view shows sliding light-tight door 150 which provides a light-tight seal to plate introduction apertures in the top of light-tight enclosure 100 located under plate stackers 120 and 122. Motor 155 is coupled via belt to a linear screw drive (not shown) that opens door 150. The views provided of plate reader 100 illustrate the use of certain specific translation mechanisms to move a variety of components of the apparatus including door 150; while the specific mechanisms chosen may have certain inventive advantages, the description is not meant to be limiting and one skilled in the art will be able to select from a variety of conventional single or multiple axis translation mechanisms. It should also be noted that to simplify the drawing, electronic circuit boards are not shown.

Imaging system 160 is mounted on an imaging aperture in the top of light-tight enclosure 110 and can image luminescence from plates in enclosure 110. Pump 170 is a used to drive fluids through the integrated pipetting system. One skilled in the art will be able to select appropriate pumps for use in the system including, but not limited to diaphragm pumps, peristaltic pumps, and syringe (or piston) pumps (as shown). Pump 170 also comprises a multi-port valve to allow the pump to push and pull fluids from different fluidic lines. Alternatively, multiple pumps can be used to independently control fluidics in different fluidic lines. A bar code reader 180 and rotating mirror 185 are used to scan bar codes from plates in input plate stacker 122. Fluidic station 200 is used to deliver sample to the apparatus, wash the integrated pipettor, and dispose of waste from the pipettor. Piercing tool 225 is used to pierce and displace seals on wells of sealed plates so as to allow for unblocked imaging of the wells. Pipetting probe translation stage 250 provides horizontal and vertical translation of dual pipetting probe 260.

Figure 3:
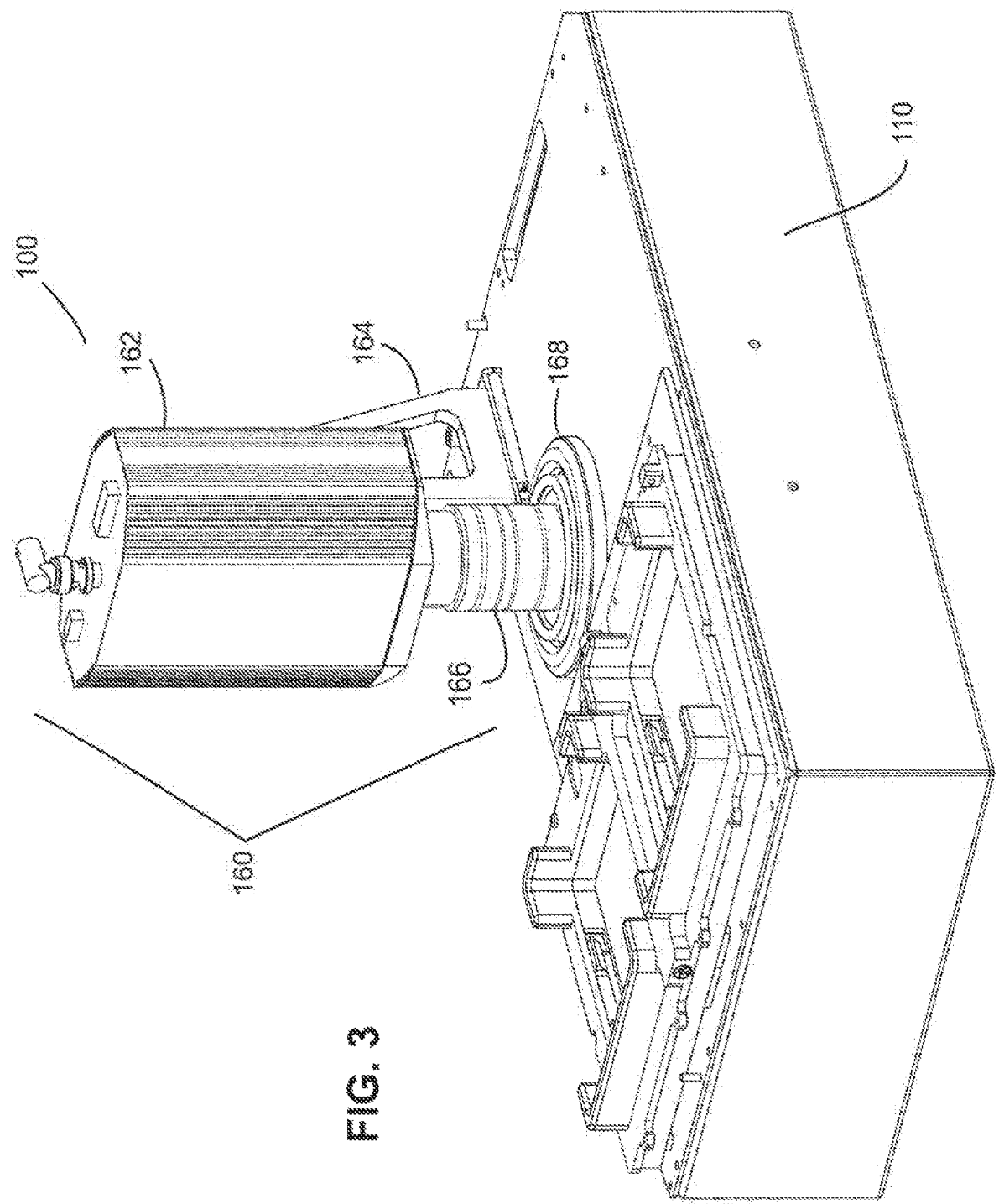
FIG. 3 shows one embodiment of a light detection system 160 of plate reader 100.
Figure 4:
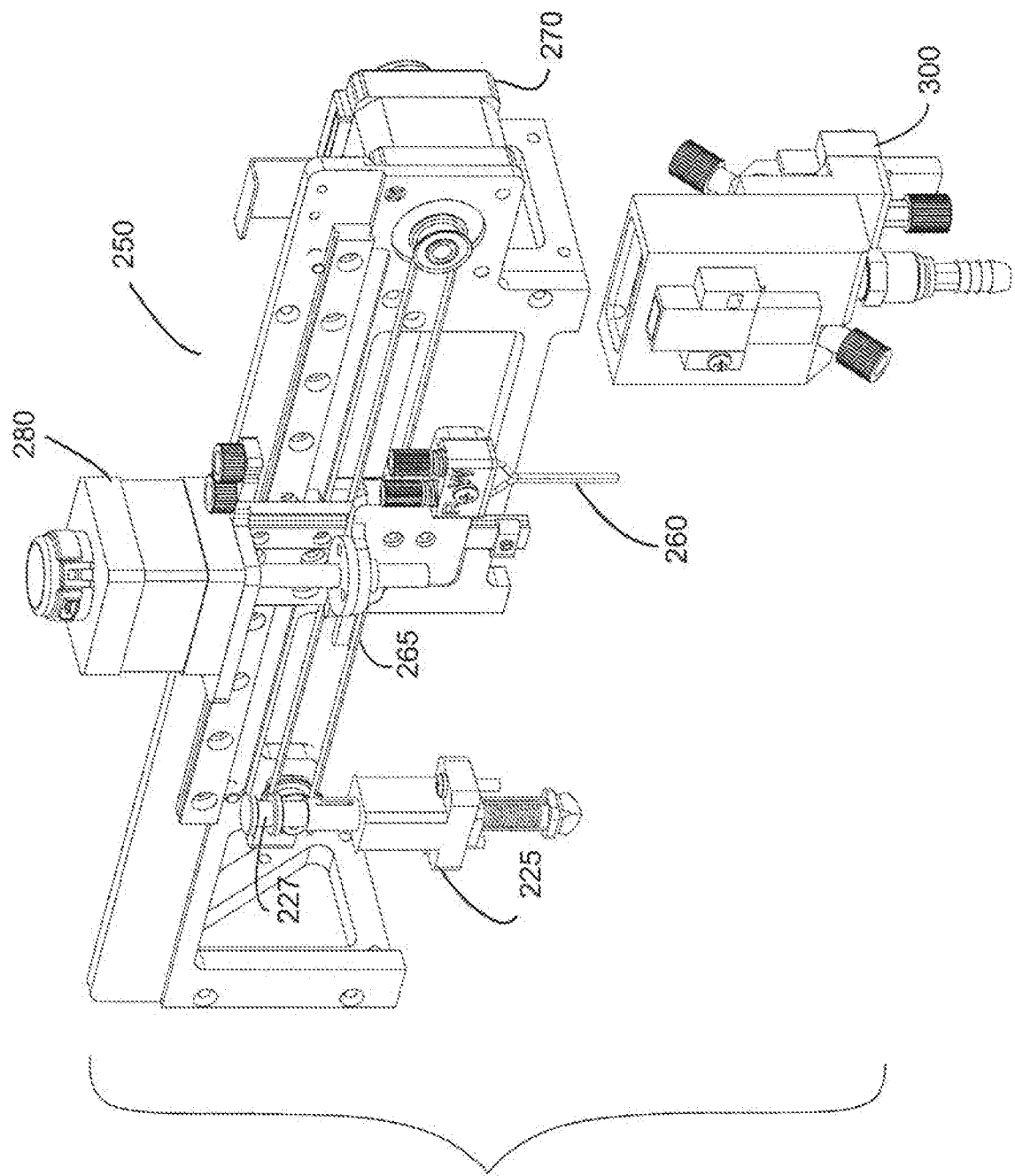
FIG. 4 shows embodiments of certain fluidic and seal piercing components.

FIG. 3 is another view of plate reader 100 that focuses on the components of imaging system 160 and shows camera 162 mounted on the top of light-tight enclosure 110 via camera bracket 164. Lens 166, coupled to camera 162, is used to provide a focused image of luminescence generated from plates in enclosure 110. Diaphragm 168 sealed to lens 166 and an aperture in the top of enclosure 110, and allows imaging system 160 to image light from enclosure 110 while maintaining enclosure 110 in a light-tight environment protected from environmental light. Suitable cameras for use in imaging system 160 include, but are not limited to, conventional cameras such as film cameras, CCD cameras, CMOS cameras, and the like. CCD cameras may be cooled to lower electronic noise. Lens 166 is a high numerical aperture lens which may be made from glass or injection-molded plastic. The imaging system may be used to image one well or multiple wells of a plate at a time. The light collection efficiency for imaging light from a single well is higher than for imaging a group of wells due to the closer match in the size of the CCD chip and the area being imaged. The reduced size of the imaged area and the increase in collection efficiency allows for the use of small inexpensive CCD cameras and lenses while maintaining high sensitivity in detection. Particularly advantageous, for their low cost and size, is the use of non-cooled cameras or cameras with minimal cooling (preferably to about −20° C., about −10° C., about 0° C., or higher temperatures). FIG. 4 shows enlarged views of plate seal piercing tool 225, pipettor translation stage 250, and sample/waste station 300. Pipettor translation stage 250 comprises dual probe pipettor 260 which is mounted on motorized vertical translation stage 280 which is, in turn, mounted on horizontal translation stage 270. Horizontal translation stage 270 uses a motor and belt drive to move vertical translation stage 280 along a linear guide rail, and moves pipettor 260 horizontally between piercing tool 225 and sample/waste station 300. Vertical translation stage 280 uses motorized linear screw drive to raise and lower dual probe pipettor 260. The range of motion allows probes 260 to access fluid in the sample/waste station and to access (through apertures in the top of light-tight enclosure 110, not shown) wells of plates located in enclosure 110.

Dual probe pipettor 260 includes fluidic connection for connecting both probes to fluidic lines. The use of two probes allows one probe to be used to deliver liquid to the wells and one probe to be used to remove waste. Alternatively, the two probes may be used to deliver to different reagents from two different fluidic lines. Vertical translation stage 280 includes piercing probe translation element 265 which is shaped to slide into slot 227 on piercing tool 225. By using pipettor translation stage 270, probe translation element may be moved so as to contact and grab piercing probe 225 at slot 227 via yoke 265. Up and down movement of vertical stage 280 can then be used to control the vertical position of piercing probe 225.

FIG. 5 shows two views of sample/waste station 300. Station 300 has three open compartments defined on its upper surface: sample compartment 310, waste compartment 320, and washing compartment 330. Sample compartment 310 is in fluidic connection with fluidic connector 312. Sample delivered to fluidic connector 312 (e.g., from an air sampling system) fills sample compartment 310 and is made available to pipettor 260. Waste compartment 320 drains to fluidic connector 322 and provides a receptacle for pipettor 260 to deliver waste. Washing compartment 330 can be used to wash the surface of pipettor 260; pipettor 260 is inserted in compartment 330 and the fluidic system is directed to dispense wash fluid which flows along the outside surface of pipettor 260 before overflowing into waste compartment 320. Compartments 310, 320, and 330 are countersunk into well 305 such that any overflow in compartments 310 and 330 is directed to waste and does not overflow station 300. Fluidic sensors 314 and 324 are included to monitor fluid levels in compartments 310 and 320, and ensure proper operation. Suitable fluid sensors include but are not limited to optical reflectance and capacitance sensors.

Reagent block 340 is simply used to provide a connection between an external liquid reagent source (connected to fluidic connector 344) and pump 170 (connected to fluidic connector 342). Reagent block 340 is monitored using fluid sensor 346 to ensure delivery of the liquid reagent. The liquid reagent may be omitted if not needed for a particular application. Non-exclusive examples of possible uses for the liquid reagent include use as a working fluid for the pump and fluid lines, as a wash buffer for washing assay wells, and/or as a read buffer for providing the optimal environment for luminescence measurements. In one embodiment, it is an electrochemiluminescence read buffer. Waste and liquid buffers may be stored in external or internal bottles. Alternatively, they may be stored in a reagent cartridge, e.g., as described herein.

One skilled in the art will understand that one or more of the functional components in sample/waste station 300 (e.g., one of the compartments, the reagent block, the sensors, etc.) may be omitted or may be provided in a separate part. In addition, the sample compartment may be complemented or replaced by other methods of providing samples. For example, a tube rack and/or source plate station may be incorporated in the instrument. Such embodiments may be configured so that the travel of probe 260 is sufficient to access such tubes or the wells of such source plates. The rack or plate holder may also have an axis of motion to help provide access to all tubes and wells. In one embodiment, the horizontal motion of the probe in the widthwise direction (i.e., from side to side relative to the base of the instrument)

and movement of the tube or plate holder in the lengthwise direction (i.e., from front to back) provides access to arrays of tubes in a tube rack and/or wells held in a source plate in a plate holder.

Figure 6C:
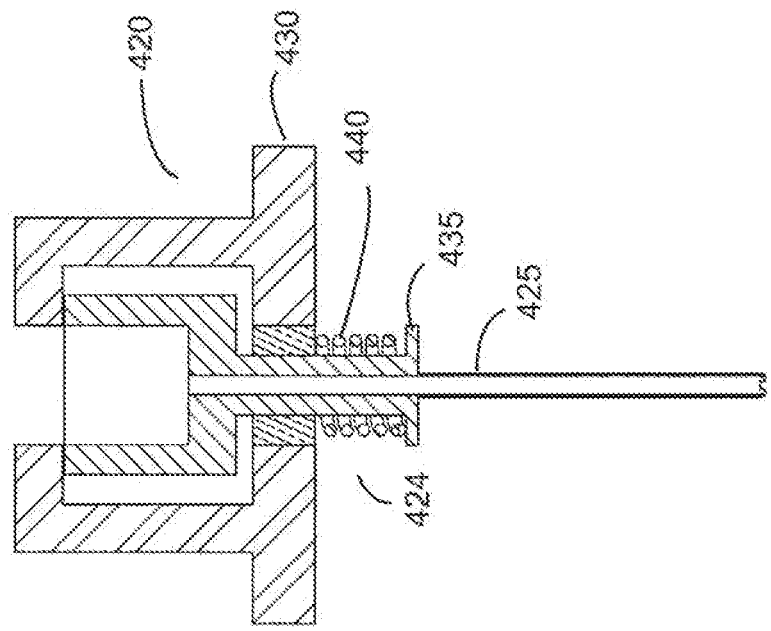
FIGS. 6a-6c show an embodiment of a spring-loaded pipette probe 400.
Figure 6B:
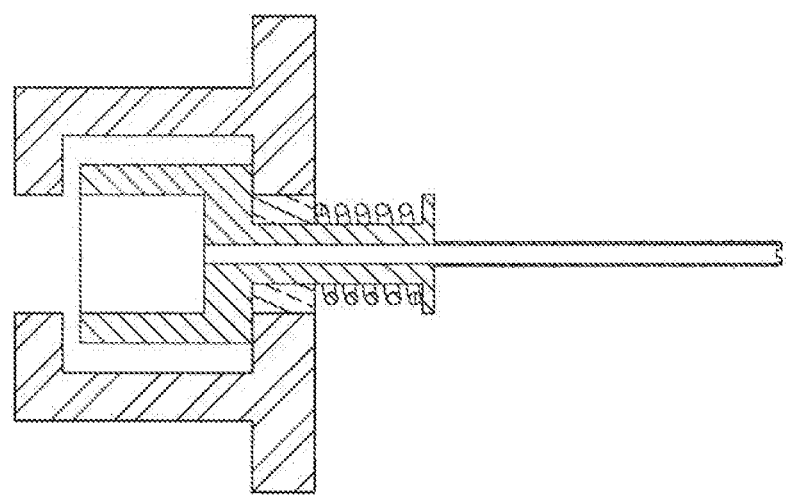
Figure 6A:
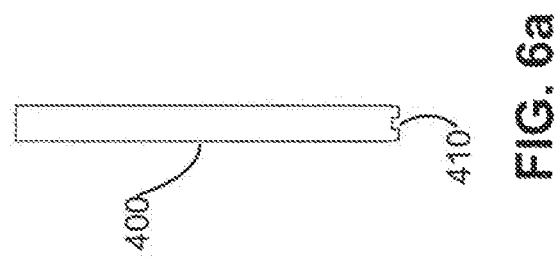

FIG. 6a shows a detailed view of a pipetting probe tip 400 which may be used on one or both of the probes on pipettor 260. Probe 400 is a hollow tube with a blunt end with slots 410 cut into the tip around the circumference of the probe, allowing for fluid to be aspirating and dispensed from the probe when the probe is in contact with a surface. Rectangular slots are shown, but it is clear that alternative geometries, including triangular or semicircular openings, may also be used. There may be one or more slots around the circumference of the probe tip. The slots may be arranged in a symmetrical pattern, or the slots may be placed on a particular side of the probe (asymmetrical) so that liquid is aspirated from a preferred direction, i.e., in order to pull liquid from a meniscus around the bottom edge of the well.

Optionally, the pipetting probes used in the apparatuses are spring loaded so that they can contact a surface without damaging the surface or the probes. FIGS. 6b and 6c show liquid dispenser 420 which shows an alternative probe embodiment that may be used. Liquid dispenser 420 comprises pipetting probe 424 having vertical tube element 425 and probe guide 430 that is configured to allows tube element 425 to move vertically in guide 430 between a fully extended position (FIG. 6b) and a fully retracted position (FIG. 6c). As shown, a large diameter region of probe 424 is confined between two position stops defined by inner surfaces of guide 430 although one skilled in the art will be able to design alternate configurations of position stops. Dispenser 420 also comprises spring element 440 which is compressed between a surface of guide 430 and ledge (or collar) 435 on vertical tube element 425 so that in the absence of external force on the bottom of the probe, said tube element stays in the extended position. The dispenser also comprises a vertical translation stage attached to guide 430 (not shown) that allows raising and lowering guide 430.

In one embodiment of a pipetting operation using dispensor 420, guide is lowered such that probe 424 is lowered into a container until it touches the bottom surface. Lowering continues such that tube element 425 pushes against spring 440, and retracts into probe guide 430 to a position between the fully extended and fully retracted positions. Fluid is added or removed from the well and probe 424 is raised out of the well. In a specific example employing a container with a piercable seal, the method may further comprise lowering the translation stage until probe 424 contacts and pierces the seal. In addition, piercing the seal may further comprise e) lowering the translation stage until pipetting probe 424 contacts the plate seal, f) continuing to lower the translation stage such that the tube element 425 pushes against spring 440 and retracts into probe guide 430 to the fully retracted position, and g) continuing to lower the translation stage such that pipetting probe 424 pierces the plate seal and tube element 425 returns to the fully extended position.

Figure 7E:
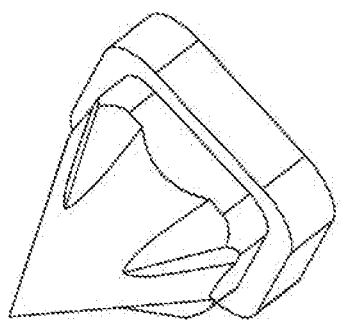
FIGS. 7e-7f show an alternative embodiment of the piercing tip that is conical and has exposed edges that extend in a radial direction from the tip.
Figure 7F:
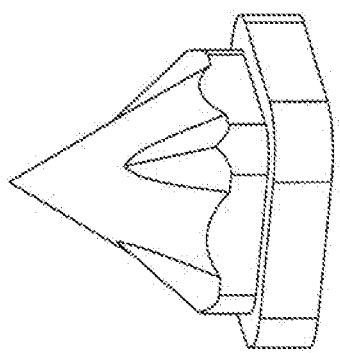

FIGS. 7a-7b show two views of piercing probe 225 from apparatus 100. Piercing probe 225 comprises a piercing section 450 with external surfaces that taper to a vertex to form piercing tip 451 at one end of a piercing direction (the direction in which the probe moves to pierce a well, in this case the long axis of the probe). Piercing probe 225 also comprises a seal displacement section 452 arranged adjacent to piercing section 450 along the piercing dimension. Displacement section 452 conforms to, but is slightly undersized, relative to the shape of the openings of the wells it is intended to pierce (in this case, square wells with rounded corners). After piercing section 450 pierces a seal, displacement section 452 pushes the plate seal against the well walls and prevents the seal from interfering with the detection of signals in the well. Piercing probe 225 also comprises plate stop section 454 adjacent to displacement section 452. Stop section 454 is sized so that it can not enter the target wells and thus defines the maximal travel of probe 225 into a target well.

As noted above, displacement section 452 conforms to the shape of the wells it is intended to pierce. The cross-sectional area (perpendicular to the piercing direction) may take on any well shape including, but not limited to, round, elliptical, polygonal (regular or not), and polygonal with rounded corners. In one specific example it is square or square with rounded edges. Piercing section 450 may take on shapes that include, but are not limited to, conical shapes and pyramidal shapes. As shown in FIG. 7a, it has a square pyramidal shape with edges 453 extending in a radial direction from tip 451. The edges of the pyramid, advantageously, form cutting edges that help to cut a seal into sections during a piercing operation. For example, the piercing probe as shown in FIGS. 7a-7b is designed to pierce a seal on a rounded square well, cut the seal diagonally to form four triangular seal sections and fold these sections against the walls of the well. Cutting edges may also be raised from the surface, e.g., piercing system may be basically conical in shape but have raised cutting edges that extend from the conical surface. An apparatus is also provided for analyzing a multi-well plate that includes a piercing probe and a sealed plate. Suitable plates include plates sealed with a sealing film (for example, an adhesive, heat sealed, or sonic welded film). The film may comprise materials including, but not limited to, plastics and metal films or a combination of both. In one specific embodiment, the seal is a metal foil (which may be coated with a sealing layer such as heat sealable or adhesive coating or film) such as a heat sealable or adhesive aluminum foil.

As shown in FIG. 7b, piercing probe 225 is spring loaded to provide a restorative force and to limit the maximum force that can be applied to a plate. Piercing probe 225 comprises a probe shaft 460 that slides within an aperture in probe guide 470, probe guide 470 being fixedly mounted on the top of light tight enclosure 110 (see FIG. 2). Compression spring 461 provides a restorative force that biases probe shaft 460 to be full raised into probe guide 470. The restorative force is provided between i) pin 464 which is fixedly held in shaft 460 and ii) pin 462 which is fixedly held between guide 470 and the top of enclosure 110 but can move freely in slot 463 of shaft 460 (slot 463 defining the range of motion of probe shaft 460 relative to guide 470). Probe 225 is designed to be moved in the piercing direction by application of force to plunger 465 (for example, by grabbing slot 227 with probe displacement element 265 (see FIG. 4) and translating probe displacement element 265 in a vertical direction). A second compression spring (not shown) between plunger 465 and pin 464 limits the force that may be applied with piercing probe 225; if excessive force is applied, the plunger will compress the second compression spring instead of moving shaft 460 relative to guide 470. Pin 466 in slot 467 defines the maximal travel of plunger 465 in shaft 460.

Figure 8:
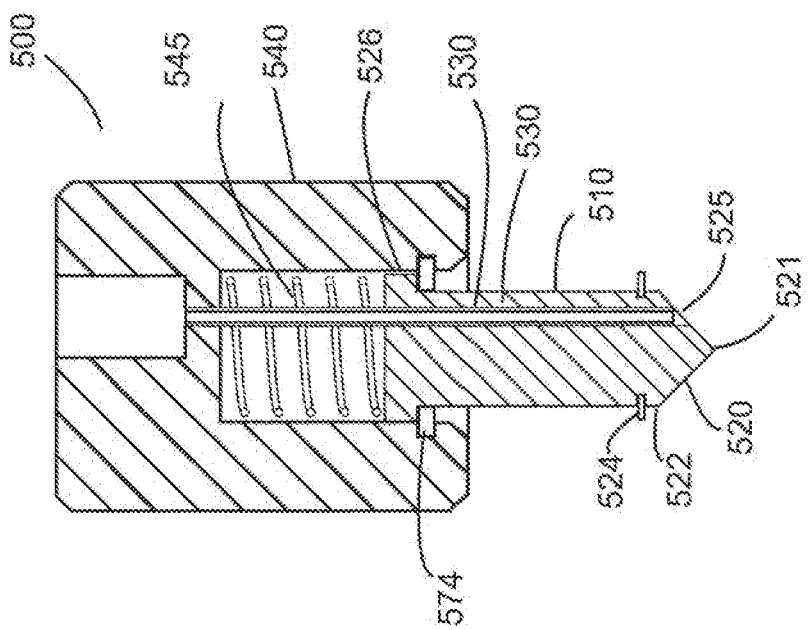
FIG. 8 shows an embodiment of an integrated plate seal piercer/pipettor 500.

FIG. 8 shows alternate embodiments of piercing and pipetting probes that are integrated into one unit. FIG. 8 shows a seal piercer/pipettor 500 that comprises a seal piercing probe 510 having a seal piercing section 520 with a seal piercing tip 521, a seal displacement section 522, and a plate stop section 524. Piercer/pipettor 500 also comprises a piercing probe guide 540 having a cylindrical opening in which probe 510 can slide along the piercing direction. Piercing probe 510 also has a through-hole 525 parallel to the piercing direction and, in one example, off-set from piercing tip 521. Pipette probe 530 is movably-located in through-hole 525 and fixedly attached to guide 540 such that movement of piercing probe 510 away from guide 540 causes pipetting probe 530 to extend from piercing probe 510, and movement of piercing probe 510 toward guide 540 causes pipetting probe 530 to withdraw into piercing probe 510. Compression spring 545 in guide 540 acts to push piercing probe 510 away from guide 540, and to retract pipetting probe 530 (the maximal displacement of piercing probe 510 being limited by physical stops, specifically collar 526 on probe 510 and ledge 547 on guide 540.

In operation, plate guide 540 is lowered toward a sealed well such that piercing probe 510 pierces and displaces the seal on the well. The spring constant of compression spring 545 is selected such that the seal can be pierced without substantial compression of spring 545 (and pipetting probe 530 remains retracted in through-hole 525 and co-translates with piercing probe 510). Continued lowering of guide 540 results in plate stop section 524 contacting the top surface of the well, preventing further translation of piercing probe 510, and resulting in compression of spring 545 and extension of pipetting prove 530 into the well.

Figure 9C:
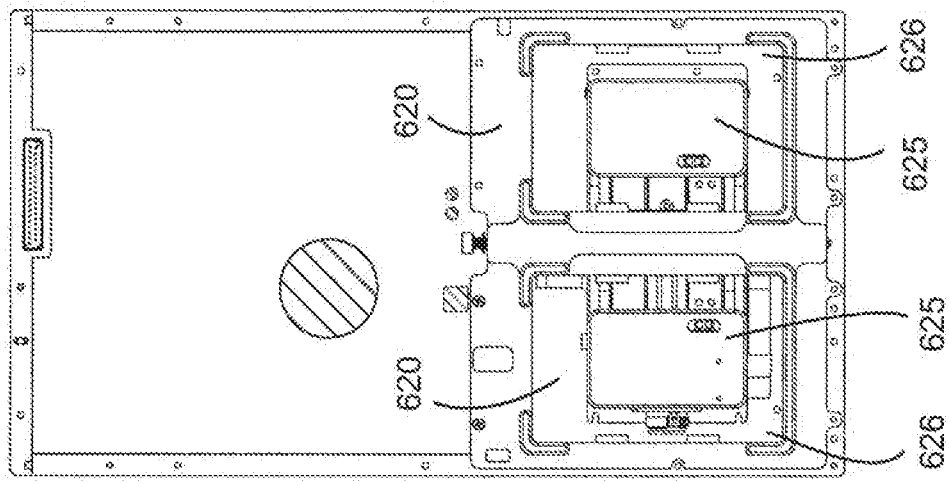
FIGS. 9a-9c show top views of an embodiment of light-tight enclosure 110 of plate reader 100 and illustrates the operation of sliding light-tight door 150 (shown in cross-hatch).
Figure 9B:
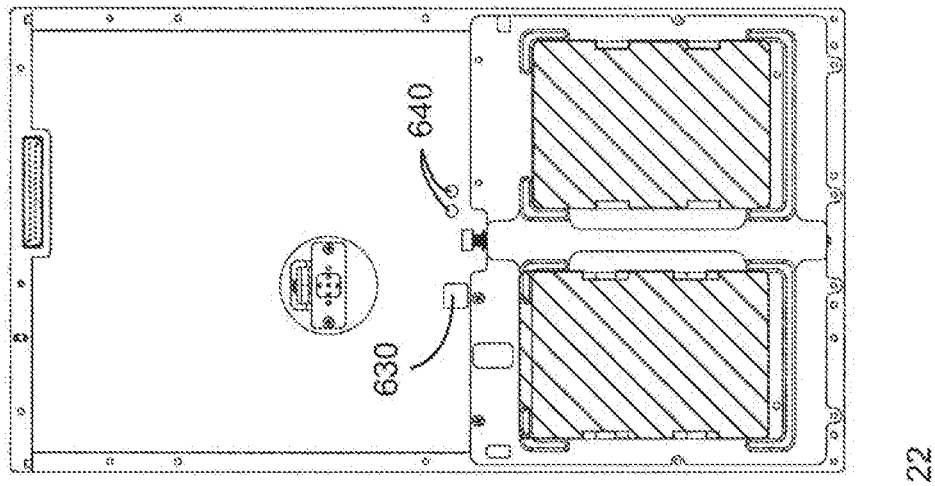
Figure 9A:
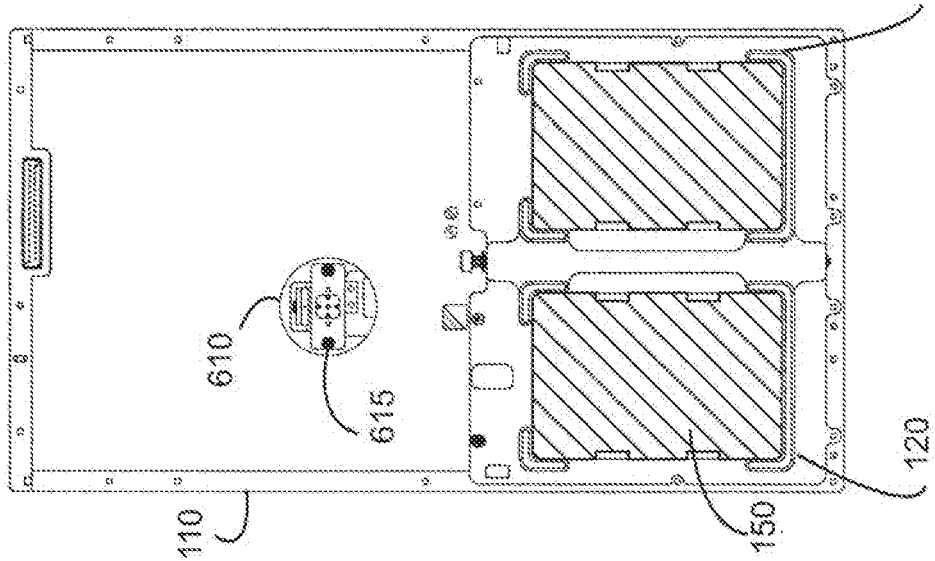

FIGS. 9a-9c show top views of light-tight enclosure 110 of apparatus 100 (see FIGS. 1-2) after removing most of the components mounted on top of enclosure 110. FIG. 9 shows three views (a-c) with sliding light-tight door 150 in three different positions (for clarity, exposed surfaces of door 150 are shown in cross-hatch). In FIG. 9a, door 150 is in the fully sealed position so as to fully seal plate introduction apertures 626, piercing probe aperture 630, and pipetting probe apertures 640 in the top of enclosure 110. Light detection aperture 610 is unblocked allowing detection and/or imaging of light emitted from wells positioned underneath aperture 610. This view also shows plate contact mechanism 615 mounted on the bottom of enclosure 110 under aperture 610. Plate contact mechanism 615 is designed for use with plates having electrodes within the wells and electrode contacts to these electrodes patterned on the bottom of the plates; plate contact mechanism 615 providing electrical contact to the electrode contacts of the wells positioned under aperture 610.

In FIG. 9b, sliding door 150 is partially opened to align piercing probe and pipetting probe apertures in sliding door 150 with corresponding apertures 630 and 640 in the top of enclosure 110. With the door in this position, the piercing and pipetting probes can access wells positioned under the appropriate apertures. Multiple pipetting apertures are provided so that a pipetting probe can access multiple locations in a well or multiple wells in plate without repositioning the plate. In FIG. 9c, sliding door 150 is fully opened, fully opening plate introduction apertures 626 and allowing the transfer of plates between plate stackers 120 and 122, and plate elevator 625.

Figure 10:
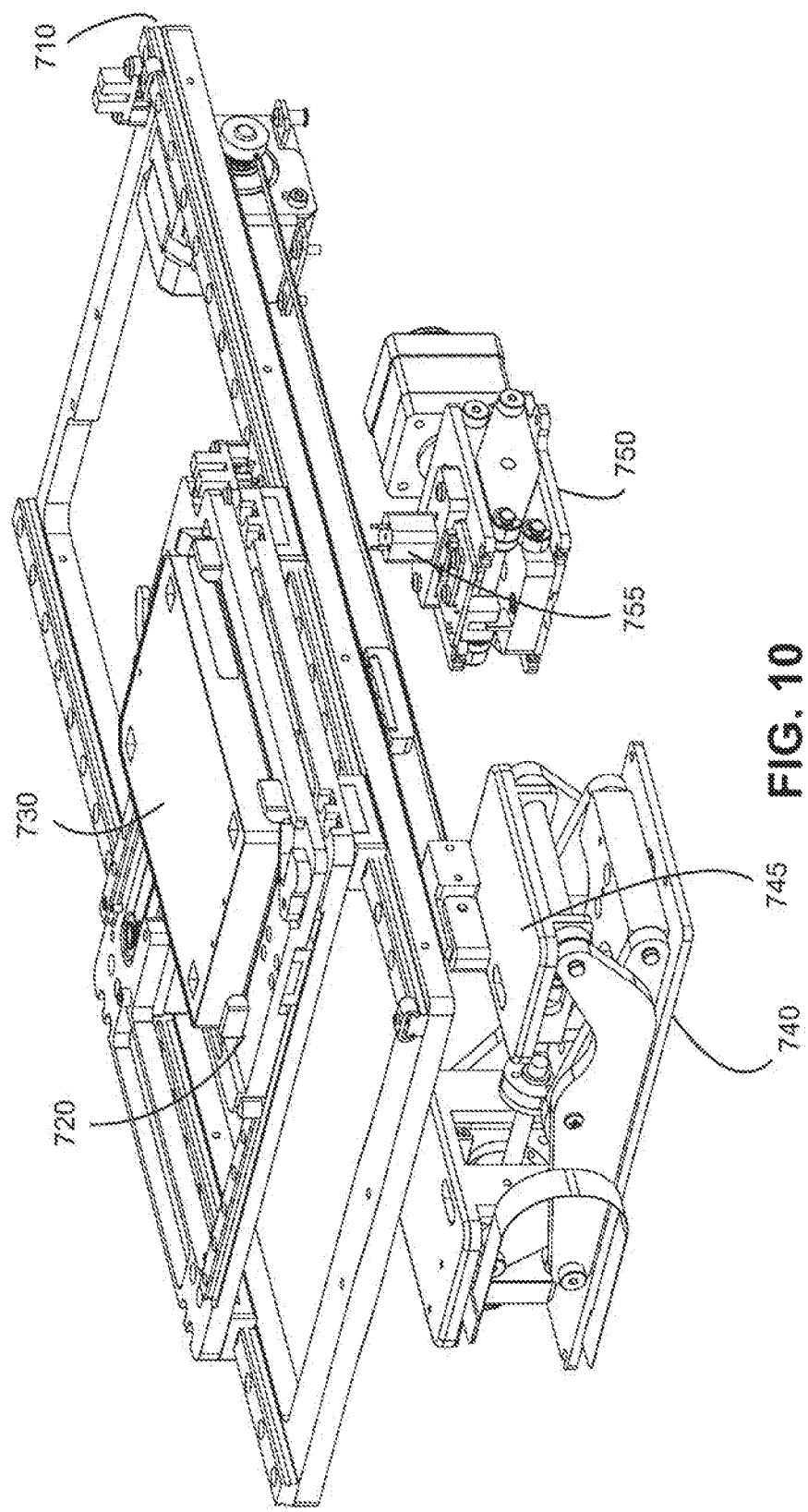
FIG. 10 shows a view of the mechanical components present in one embodiment of light-tight enclosure 110 of plate reader 100.

FIG. 10 shows the mechanical components present in light-tight enclosure 110. Plate translation stage 710 is mounted at an elevated position within enclosure 110, and provides a plate holder 720 and holding plate 730. Translation stage 710 comprises linear guides and motors that provide two horizontal axis of translation to plate holder 720, and allows plate holder 720 to cover most of the horizontal area with enclosure 110. Plate holder 720 supports plate 730 at the edges and is open in the center so that plate elevator 740 and contact mechanism 750 may contact the bottom of plate 730 through plate holder 720. When plate holder 720 is positioned over one of platforms 745 on elevator 740, the motor driven scissor mechanism of elevator 740 may operate to raise the platform, and lift plate 730 from plate holder 720 and up to a plate stacker mounted on the top of enclosure 110. Similarly, when plate holder 720 is positioned over contact mechanism 750, the motor driven scissor mechanism of contact mechanism 750 may operate to raise electrical contacts 755 so that they contact electrode contacts on the bottom of plate 730, and allow application of electrical energy, through said contacts, to electrodes in the wells of plate 730, for example, to induce electrochemiluminescence at those electrodes. It should be noted that the motion systems described for moving plates, electrical contacts, probes, etc. are not limited to the specific mechanisms depicted herein, although these mechanisms may have specific advantages. It is well within the purview of one in the art to select other conventional mechanism for accomplishing the desired movement of components.

In one embodiment, translation stage 710 may be used to achieve rapid one or two axis oscillation of plate holder 720 and, thereby, to shake and mix the contents of a plate on the plate holder. The shaking profiles can range from continuous single-axis shaking to duty-cycled orbital shaking. One example includes shaking with the axes at two different frequencies. The system may also provide for sonication to enhance mixing during sample incubation, for example, as described in the U.S. Pat. No. 6,413,783 of Wohlstadter et al.

In one embodiment, the light tight enclosure includes a light source located underneath the imaging aperture and below the elevation of the plate holder. This arrangement allows for the use of fiducial holes or windows in plates to be used to correct for errors in plate alignment. Light from the light source is passed through the fiducials and imaged on the imaging system so as to determine and correct for the alignment of the plate. Advantageously, plates formed from plate bottoms mated to a plate top (e.g., plates with screen printed plate bottoms mated to injection-molded plate tops as described in copending U.S. application Ser. Nos. 10/185, 274 and 10/185,363) advantageously include fiducials patterned (e.g., screen printed) or cut into the plate bottom to correct for misalignment of the plate bottom relative to the plate top. In one specific embodiment, the plate top on such a plate includes holes (e.g., in the outside frame of the plate top) aligned with fiducials on the plate bottom to allow imaging of the fiducials. Accordingly, the imaging of light generated under a plate may be used to communicate the exact position of the plate to the image processing software and also to provide for a camera focus check. The plate may then be realigned using a two-axis positioning system. Thus, a plate positioning method is provided comprising: (1) providing a plate having light-path openings; (2) illuminating plate from the bottom; (3) detecting light coming through light-path openings; and (4) optionally, realigning the plate.

The apparatuses, systems, method, reagents, and kits may be used for conducting assays on environmental samples. They may be particularly well-suited for conducting automated sampling, sample preparation, and analysis in the multi-well plate assay format.

One embodiment is an autonomous environmental monitoring system comprising (1) a sample collection module; (2) optionally, a sample processing module; and (3) a biological agent detection module, wherein the modules are fluidically connected, or in one example connectable, to allow for sample transfer between modules. According to one embodiment, an autonomous environmental system allows for multi-week periods of sustained operation requiring reduced human interaction.

The biological agents that may be detected include viral, bacterial, fungal, and parasitic pathogens as well as biological toxins. The agents themselves may be detected or they may be detected through measurement of materials derived from the agents including, but not limited to, cellular fragments, proteins, nucleic acids, lipids, polysaccharides, and toxins.

In one embodiment, the autonomous environmental monitoring system samples air, suspends particulate matter from the air sample in a collection fluid thereby creating a liquid sample, and performs an assay for one or more biological agents including viruses, bacteria, and toxins. The assay can be conducted in a singular or multiplexed assay format.

Some examples of biological agents include, but are not limited to, vaccinia virus, *Brucella* spp., botulinum toxin A, ricin, staph enterotoxin B (SEB), Venezuelan equine encephalitis (VEE), *Yersinia pestis* (YP), *Bacillus anthracis* (BA), *Coxiella burnetii* (CB), and *Francisella tularensis* (FT).

In one embodiment, the system also comprises a computer that receives and processes data from a biological agent detection module. The computer recognizes in the data the positive identifications and, optionally, increases the frequency of conducting tests, transmits the data to alert the appropriate authorities, and further, optionally, automatically alerts nearby additional autonomous environmental monitoring system which automatically increase frequency of analysis and/or lower detection limits to identify presence of biological agents.

Thus, a network is also provided of autonomous environmental monitoring systems. According to one embodiment, each autonomous environmental monitoring system in the network may automatically determine individualized detection threshold limits by accounting for the background data at individual sites through acquiring sampling of the background at that specific location over the period of operation. The acquired background level information is used to track average background level and the standard deviations of the background level, and dynamically adjust the detection thresholds limit for a site location of an individual autonomous environmental monitoring system.

According to one embodiment, a sample collection module is capable of collecting and processing environmental samples such as suspensions of particles filtered, or otherwise concentrated, out of air samples. Air sampling systems that may be used include filter based collectors, impactors, virtual impactors, and wetted cyclones. Examples of standard sample collection modules that can be used include systems described in U.S. Pat. Nos. 6,888,085; 6,887,710; 6,867,044; and 6,567,008. Additionally, or alternatively, the sample collection module may be configured to collect, concentrate, and/or process other classes of samples such as water samples, soil samples, clinical samples, environmental swipes, etc., environmental sludges, food samples, beverages, samples that comprise suspensions of dirt, or biological samples. Clinical samples that may be analyzed include, but are not limited to, feces, mucosal swabs, physiological fluids and/or samples containing suspensions of cells. Specific examples of biological samples include blood, serum, plasma, tissue aspirates, tissue homogenates, cell cultures, cell culture supernatants (including cultures of eukaryotic and prokaryotic cells), urine, and cerebrospinal fluid.

A device for suspending particulate contained in the aerosolized particulate stream in a collection fluid may utilize a sonicator, a vortex mixer, a shaker, a simple mixer, or other means for optimizing contact between a fluid and an air sample.

According to one embodiment, a surfactant can be added to the collection fluid to prevent loss of biological agents to particles (including, but not limited to, paper, debris, and dust) in the collector solution. Useful surfactants include, but are not limited to ionic or non-ionic detergents or surfactants (e.g., classes of non-ionic detergents/surfactants are known by the trade names of BRIJ, TRITON, TWEEN, THESIT, LUBROL, GENAPOL, PLURONIC, TETRONIC, and SPAN). According to another embodiment, biological agents adsorbed on particulate, for example cellulose-based debris, are released back into solution by treatment with a carboxylic acid, for example, acetic acid, or citric acid.

According to one embodiment, detection of biological agents is improved by physical or chemical processing of the sample. The processing can be used to (1) concentrate biological agents in the sample, (2) lyse and/or fragment the biological agents, and (3) expose binding sites that would otherwise remain inaccessible.

A device may include a concentrator system to concentrates biological agents suspended in the liquid sample by filtration, affinity separation and/or centrifugation. The filtration concentrator system may employ a filter selected to retain bacterial and viral particles while excising excess fluid. In one example, filtration concentrator system employs filters that retain biological molecules, such as proteins, toxins, nucleic acids, polysaccharides, and lipids. The system may also provide for biological agent removal from the filter and re-suspended in solution, for example by flowing buffer solution in the reverse direction and/or sonication.

The centrifugation concentrator system separates biological agents from the fluid by removing excess fluid following the centrifugation. The system also provides for re-suspension of the concentrated biological agents in a smaller volume of fluid following excess fluid removal.

According to one embodiment, the system employs affinity concentration unit comprising an affinity resin capable of binding to biological agents. Examples of the affinity resin include, but are not limited to, hydrophobic interaction resins (C4-C18, poly-, polyethyl-, and polymethyl-aspartamide). The resin can be conveniently packaged in columns, cartridges, or used as loose beads. The system provides for biological agents removal from the affinity media by elution with a release solvent.

According to one embodiment, at least one analyte can be concentrated through immobilization on the surface of at least one microparticle, or a plurality of microparticles (for example, a plurality of magnetically responsive microparticles), either passively (e.g., by non-specific binding) or via binding interactions with a binding partner of the analyte (e.g., an antibody that binds the analyte) or via chemical linkage such as via covalent bonds (e.g., reaction with an NETS-ester) and/or by reaction with an appropriate linker, or via one or more specific binding reagents, and/or by a combination thereof.

In one embodiment, an ultrasonic lysis system is incorporated into the sample processing module, e.g., a system as described in U.S. Pat. No. 6,413,873 of Wohlstadter et al. Alternatively, the sample processing module may comprise a chemical lysis system. Chemical lysis by detergents, acids, bases, or other lysing agents can be used to break open vegetative bacteria, spores, and viral particles. An acidic or basic solution used for chemical lysis can then be neutralized prior to sample delivery to the analyte detection module. According to one embodiment, lysis system is incorporated upstream of a separator comprising a concentrator system. Alternatively, lysis follows removal of biological agents from a concentrator unit.

The sample processing module may further include a partial purification system, capable of removal of undesirable and in some examples interfering matter. For example, the partial purification system may include a filter permeable to biological molecules, but impervious to large particulate. The module may also include a chemical partial purification system (for example, a system for precipitating nucleic acids using alcohols).

According to one embodiment, a biological agent detection module comprises a reader for reading electrochemiluminescence (ECL) from multi-well plates. For example, ECL-based multiplexed testing is described in U.S. Publications 2004/0022677 and 2004/0052646 of U.S. application Ser. Nos. 10/185,274 and 10/185,363, respectively; U.S. Publication 2003/0207290 of U.S. application Ser. No. 10/238,960; U.S. Publication 2003/0113713 of U.S. application Ser. No. 10/238,391; U.S. Publication 2004/0189311 of U.S. application Ser. No. 10/744,726; and U.S. Publication 2005/0142033 of U.S. application Ser. No. 10/980,198.

In one embodiment, the biological agent detection module has an integrated pipettor and a fluidic manifold for receiving samples and buffers, and distributing them to the wells of a plate. According to one preferred embodiment, the module allows to induce and measure ECL from only one well at a time.

One example of the analyte detection module, picture in FIG. 1, demonstrates the arrangement in a compact instrument of a mechanical system for storing and moving plates, a light detector for measuring luminescence (including ECL), a fluidic interface and pipetting system for transferring samples to the plates, and the electronic boards that drive the module.

According to one embodiment, the analyte detection module has three subsystems: (1) light detection, (2) liquid handling, and (3) plate handling. Each subsystem may, optionally, have a built-in error detection component to ensure reliable operation and to reduce the probability of false positives.

A method is also provided for conducting assays for biological agents including, but not limited to, biological warfare agents. In one embodiment, the method is a binding assay. In another embodiment, the method is a solid-phase binding assay (in one example, a solid phase immunoassay) and comprises contacting an assay composition with one or more binding surfaces that bind analytes of interest (or their binding competitors) present in the assay composition. The method may also include contacting the assay composition with one or more detection reagents capable of specifically binding with the analytes of interest. The multiplexed binding assay methods according to preferred embodiments can involve a number of formats available in the art. Suitable assay methods include sandwich or competitive binding assays format. Examples of sandwich immunoassays are described in U.S. Pat. Nos. 4,168,146 and 4,366,241. Examples of competitive immunoassays include those disclosed in U.S. Pat. Nos. 4,235,601; 4,442,204; and 5,208,535 to Buechler et al. In one example, small molecule toxins such as marine and fungal toxins can be advantageously measured in competitive immunoassay formats.

Binding reagents that can be used as detection reagents, the binding components of binding surfaces and/or bridging reagents include, but are not limited to, antibodies, receptors, ligands, haptens, antigens, epitopes, mimitopes, aptamers, hybridization partners, and intercalaters. Suitable binding reagent compositions include, but are not limited to, proteins, nucleic acids, drugs, steroids, hormones, lipids, polysaccharides, and combinations thereof. The term "antibody" includes intact antibody molecules (including hybrid antibodies assembled by in vitro re-association of antibody subunits), antibody fragments, and recombinant protein constructs comprising an antigen binding domain of an antibody (as described, e.g., in Porter & Weir, *J. Cell Physiol.*, 67 (Suppl 1):51-64, 1966; Hochman et al., *Biochemistry* 12:1130-1135, 1973; hereby incorporated by reference). The term also includes intact antibody molecules, antibody fragments, and antibody constructs that have been chemically modified, e.g., by the introduction of a label.

Measured, as used herein, is understood to encompass quantitative and qualitative measurement, and encompasses measurements carried out for a variety of purposes including, but not limited to, detecting the presence of an analyte, quantitating the amount of an analyte, identifying a known analyte, and/or determining the identity of an unknown analyte in a sample. According to one embodiment, the amounts the first binding reagent and the second binding reagent bound to one or more binding surfaces may be presented as a concentration value of the analytes in a sample, i.e., the amount of each analyte per volume of sample.

Analytes may be detected using electrochemiluminescence-based assay formats. Electrochemiluminescence measurements are preferably carried out using binding reagents immobilized or otherwise collected on an electrode surface. Especially preferred electrodes include screen-printed carbon ink electrodes which may be patterned on the bottom of specially designed cartridges and/or multi-well plates (e.g., 24-, 96-, 384- etc. well plates). Electrochemiluminescence from ECL labels on the surface of the carbon electrodes is induced and measured using an imaging plate reader as described in copending U.S. application Ser. Nos. 10/185,274 and 10/185,363 (both entitled "Assay Plates, Reader Systems and Methods for Luminescence Test Measurements", filed on Jun. 28, 2002, hereby incorporated by reference). Analogous plates and plate readers are now commercially available (MULTI-SPOT® and MULTI-ARRAY™ plates and SECTOR® instruments, Meso Scale Discovery, a division of Meso Scale Diagnostics, LLC, Gaithersburg, Md.).

In one embodiment, antibodies that are immobilized on the electrodes within the plates may be used to detect the selected biological agent in a sandwich immunoassay format. In another embodiment, microarrays of antibodies, patterned on integrated electrodes within the plates, will be used to detect the plurality of the selected biological agents in a sandwich immunoassay format. Accordingly, each well contains one or more capture antibodies immobilized on the working electrode of the plate and, optionally, in dry form labeled detection antibodies and all additional reagents necessary for analysis of samples, and for carrying out positive and negative controls. In one example, arrays having multiple binding surfaces within a single well allow to replicate tests to significantly reduce false positive identification.

A positive control method is provided to identify conditions or samples that may cause false negative measurements by interfering with the generation of signal. According to this aspect, positive control method comprises contacting sample with a binding reagent (e.g., an antibody) to a positive control substance (for example, to a non-toxic positive control substance) that is not expected to be observed in environmental samples; then contacting the sample with a labeled detection reagent (for example, an antibody) against the positive control substance and a controlled amount of the positive control substance, and measuring the signal. The positive control should, therefore, always provide a constant positive signal regardless of the sample. A significantly reduced signal may indicate that the sample interferes with the antibody binding reactions or the signal generating process, or may indicate a malfunction in the plate or instrument.

A negative control method is provided employing a capture reagent (e.g., an antibody) that is not matched with a detection reagent. The method comprises contacting a sample with a capture reagent in the presence of mismatched detection reagent and measuring signal. The negative control should, therefore, provide a negative signal regardless of the sample. A significantly elevated signal from the negative control indicates the presence of a material in the sample, such as a cross-linking agent, that is causing the non-specific binding of non-matched detection reagents to the negative control capture reagent.

A method is provided using a mixture of non-specific antibodies from the same species (e.g., polyclonal mouse, rabbit, goat, etc.) as specific capture antibodies to identify any non-specific binding effects that would otherwise provide false positive identification. This mixture may be selected to include the species of the antibodies used in the actual test measurements.

A method is provided using at least two different pairs of capture and detection reagents (e.g., antibodies) in alternating independently addressable wells to reduce the frequency of false positive identifications. Accordingly, the first binding reagent pair is used as a primary to identification, which, if positive, triggers the confirmation test using the second binding reagent pair. The pairs may target the same marker or epitopes of a biological agent or, alternatively, they may further increase the orthogonality of the two measurements by targeting different markers or epitopes of a biological agent. An arrangement of at least two different antibody pairs in alternating well may be particularly advantageous. According to this aspect, the pairs are alternating as a primary identification set, thereby eliminating the need to dedicate wells as confirmation tests. Instead, if a sample is suspected to be positive based on the most recent test (based on either the first or the second pair), confirmation is simply performed by running the subsequent test well.

The reliability of detection method may be further improved by providing two or more different capture antibodies in a single well, wherein (a) the two or more different antibodies recognize the same marker and/or epitope of the same biological target; and/or b) the two or more different antibodies recognize different markers and/or epitopes of the same biological target.

One method for the detection of biological agents comprises (1) collecting an air sample using sample collection module (by the way of example, collecting aerosols in an air sample by using integrated an aerosol sampling system); (2) suspending the aerosols in a liquid; (3) optionally, transferring the aerosol suspension into a sample processing module; (4) optionally, concentrating and/or partially purifying the aerosol in the sample processing module (by the way of example, partially purifying by removing large particles); (5) transferring a liquid sample to a well of a multi-well plate, (6) adding at least one detection antibody against the same agents; (7) conducting an assay measurement and identifying samples that are positive for a biological agent; (8) optionally, performing a confirmation test by repeating (5)-(7); and (9) issuing an alert warning. Optionally, detection reagents are present in the wells in dry form and (6) may be omitted. In this case, addition of the sample results in reconstitution of the dried reagents. In one embodiment, step (5) includes transferring the sample to the well through the use of an integrated pipetting system.

Step (5) may comprise pumping the liquid sample into a sample chamber (e.g., sample compartment 310 of instrument 100) and using a pipetting system (e.g., probe 260 of instrument 100) to transfer the sample to a well of a plate), e.g., a plate in light-tight enclosure 110 of instrument 100). In one embodiment, instrument 100 as described above is used to carry out this operation as well as one or more (or all) of the subsequent analysis steps ((6)-(9)).

In one embodiment, the plate has an immobilized array of binding reagents (e.g., antibodies or nucleic acids) and bioagents in the sample bind to the corresponding immobilized reagent and a corresponding labeled detection reagent to form a sandwich complex. In some, the array is formed on an electrode and detection is carried out using an ECL measurement. In one embodiment, after addition of an ECL read buffer, labels on the electrode are induced to emit ECL by applying a voltage to the working electrode, and the emitted ECL is imaged with a CCD camera. Optionally, washing may be added prior to the ECL measurement to provide advantages in assay sensitivity, particularly for optically turbid samples generated by aerosol samplers in dirty environments. Image analysis is used to determine the location of the emitted light on the array and, thus, the identity of the agents in the sample. Image analysis also provides the intensity of the emitted light from each element of the antibody array and allows for precise quantitation of each bioagent.

Patents, patent applications, and publications cited in this disclosure are incorporated by reference in their entirety.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the claims.

A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

We claim:

1. An apparatus for measuring signals from wells of sealed multi-well assay plates, the apparatus comprising:
   (a) a sealed multi-well assay plate;
   (b) a seal removal tool for removing seals from wells of said multi-well plates, wherein said seal removal tool comprises: (1) a piercing probe with a seal piercing tip and configured to move along an axis in a piercing direction to pierce a seal of the sealed multi-well assay plate, (2) a piercing probe guide having an opening formed therein along which the piercing probe slides in said piercing direction, and (3) a through-hole provided in said piercing probe and parallel to said axis and off-set from said piercing tip;

(c) a pipetting probe that is attached to the piercing probe guide and movably located in said through-hole such that it can be withdrawn into said piercing probe during seal removal operations and extended from said piercing probe during pipetting operations; and (d) a spring disposed in the opening in the piercing probe guide and arranged to couple said piercing probe guide to said piercing probe, wherein said spring urges the piercing probe away from the piercing probe guide along said piercing direction.

2. The apparatus according to claim 1, wherein the spring has a spring constant selected such that said pipetting probe does not extend from the through-hole when said piercing probe is fully withdrawn from said wells, and translation of said pipetting probe towards said wells results in cotranslation of said piercing probe and delivery of sufficient force to remove seals on said wells.

3. The apparatus according to claim 2, wherein the spring constant is selected such that further continued translation past a maximal distance of travel of said piercing probe results in compression of the spring and extension of said pipetting probe from the through-hole into said wells.

4. The apparatus according to claim 1, wherein the pipetting probe is attached fixedly to the piercing probe guide.

5. The apparatus according to claim 1, wherein the sealed multi-well assay plate comprises wells that are square or square with rounded corners.

6. The apparatus according to claim 1, wherein the piercing probe comprises a piercing section with external surfaces that taper to a vertex so as to form said piercing tip at one end of a piercing direction, wherein said piercing section is pyramidal and said piercing section includes exposed cutting edges extending in a radial direction from said piercing tip, wherein said exposed cutting edges are positioned in said piercing section to align with the corners of said wells.

7. The apparatus according to claim 6, wherein the piercing probe further comprises a seal displacement section, arranged adjacent to said piercing section along said piercing direction, with a cross-sectional shape, perpendicular to said piercing direction, that is square or square with rounded corners, and slightly undersized relative to said wells.

8. The apparatus according to claim 7, wherein the piercing probe further comprises a plate stop section adjacent to said seal displacement section, wherein said plate stop section is sized to prevent entry of the stop section into said wells, thereby defining a maximal distance of travel of said piercing probe into said wells.

9. The apparatus of claim 1, wherein said piercing probe is spring loaded such that a maximum downward force, along said piercing direction, of said piercing probe on the plate seal is defined by a spring constant of said spring.

10. The apparatus of claim 1, wherein movement of said piercing probe and said pipetting probe are controlled independently.

11. The apparatus of claim 1, wherein said seal displacement section is slightly undersized relative to said wells to allow said piercing section to enter the wells, to cut the seal into sections during piercing, and to fold said sections against each well's internal wall.

12. A method of detecting a signal from wells of a multi-well plate using a seal removal tool for removing seals from said wells, a pipetting probe, and a spring; wherein said seal removal tool comprises (1) a piercing probe with a seal piercing tip and configured to move along an axis in a piercing direction to pierce a seal of the sealed multi-well assay plate, (2) a piercing probe guide having an opening formed therein along which the piercing probe slides in said piercing direction, and (3) a through-hole provided in said piercing probe and parallel to said piercing direction and off-set from said piercing tip, and wherein said piercing probe guide is coupled to said piercing probe by said spring;

wherein said piercing probe guide has an opening formed therein along which the piercing probe slides in said piercing direction;

wherein said pipetting probe is attached to the piercing probe guide and movably located in said through-hole such that it can be withdrawn into said piercing probe during seal removal operations and extended from said piercing probe during pipetting operations; and wherein said spring is disposed in the opening in the piercing guide probe, said spring urging the piercing probe away from the piercing probe guide along said piercing direction;

the method comprising:
(a) providing said seal removal tool;
(b) piercing, with said piercing probe, a seal on a well of said multi-well plate;
(c) extending said pipetting probe from said piercing probe;
(d) pipetting, from said pipetting probe, sample and/or assay reagent into said well;
(e) pipetting, from said pipetting probe, assay reagent into said well; and
(f) detecting said signal from said well.

13. The method according to claim 12, wherein the piercing the seal comprises cutting said seal into sections and folding said sections against each well's internal wall.

14. The method according to claim 12, wherein the piercing the seal comprises withdrawing said pipetting probe into said piercing probe during said removal.

15. The method according to claim 12, further comprising configuring the spring to have a spring constant selected such that
(i) said pipetting probe does not extend from the through-hole when said piercing probe is fully withdrawn from said well,
(ii) translation of said pipetting probe towards said well results in cotranslation of said piercing probe and delivery of sufficient force to remove a seal on said well, and
(iii) continued translation past a maximal distance of travel of said piercing probe results in compression of the spring and extension of said pipetting probe from the through-hole into said well.

16. The method of claim 12 further comprising:
washing said well,
illuminating said well, or
applying an electrical potential to said well.

17. The method of claim 12 further comprising repeating said method on one or more additional wells of said plate.

18. The method of claim 12 further comprising washing said well.

19. The method of claim 12 further comprising illuminating said well.

20. The method of claim 12 further comprising applying an electrical potential to said well.

* * * * *